United States Patent [19]
Green

[11] Patent Number: 5,928,137
[45] Date of Patent: Jul. 27, 1999

[54] SYSTEM AND METHOD FOR ENDOSCOPIC IMAGING AND ENDOSURGERY

[76] Inventor: Philip S. Green, 820 Miranda Green, Palo Alto, Calif. 94306

[21] Appl. No.: 08/841,167
[22] Filed: Apr. 29, 1997

Related U.S. Application Data

[60] Provisional application No. 60/016,830, May 3, 1996, and provisional application No. 60/021,559, Jul. 11, 1996.
[51] Int. Cl.$^6$ ........................................................ A61B 1/04
[52] U.S. Cl. .......................... 600/160; 600/104; 600/106; 600/111
[58] Field of Search ..................................... 600/101, 102, 600/104, 106, 109, 112, 160; 348/65, 71, 74, 75

[56] References Cited

U.S. PATENT DOCUMENTS

| D. 358,471 | 5/1995 | Cope et al. ............................. D24/137 |
| 3,945,371 | 3/1976 | Adelman ................................. 600/121 |
| 4,471,766 | 9/1984 | Terayama . |
| 4,538,594 | 9/1985 | Boebel et al. . |
| 4,604,992 | 8/1986 | Sato ....................................... 600/108 |
| 4,742,819 | 5/1988 | George ...................................... 128/6 |
| 4,756,309 | 7/1988 | Sachse et al. . |
| 4,879,992 | 11/1989 | Nishigaki et al. . |
| 5,178,536 | 1/1993 | Werly et al. ............................ 433/29 |
| 5,222,477 | 6/1993 | Lia . |
| 5,373,317 | 12/1994 | Salvati et al. . |
| 5,667,472 | 9/1997 | Finn et al. . |
| 5,667,473 | 9/1997 | Finn et al. . |
| 5,667,478 | 9/1997 | McFarlin et al. . |

FOREIGN PATENT DOCUMENTS 4102437   4/1992   Japan .
9315648   8/1993   WIPO .

OTHER PUBLICATIONS

Endoscopic Surgery (book), 1991, R. A. White & S.R. Klein Mosby Year Book pp. 42–43.
Operative Laparoscopic System, 1994, Circon–ACMI product literature.
Adolescent Bronchoscope, Jan. '90, Karl Storz product literature.
EndoView Brochure undated Urohealth Co.

*Primary Examiner*—John P. Leubecker
*Attorney, Agent, or Firm*—Beyer & Weaver, LLP

[57] ABSTRACT

A video image display is attached to a video endoscopic surgical component such as video endoscope, an endoscopic surgical instrument, a carrier for coupling the endoscope and the instrument, or a cannula through which the endoscope or the instrument is passed into a body part. Attachment is by means of an attachment mechanism which may be adjusted to enable the display position to be varied with respect to the component to which it is attached. According to another embodiment, a carrier in the form of an elongated tube is employed to combine and relate the movement of the endoscope and endosurgical instrument, which, by means of the carrier, may be jointly inserted into a body part either directly or through a cannula, enabling the surgeon to operate both the endoscope and the instrument with a single hand. A video display attached to the endoscope or carrier and positioned near the instrument actuation handle provides the surgeon with a visual perspective similar to that encountered in open surgery.

35 Claims, 16 Drawing Sheets

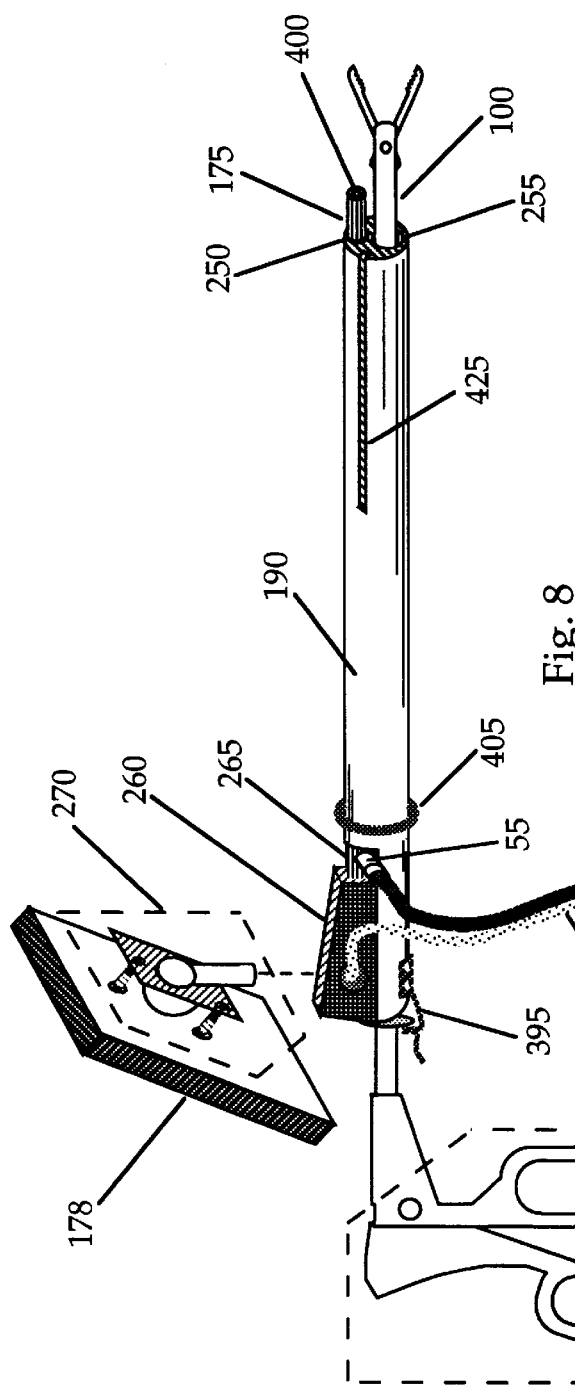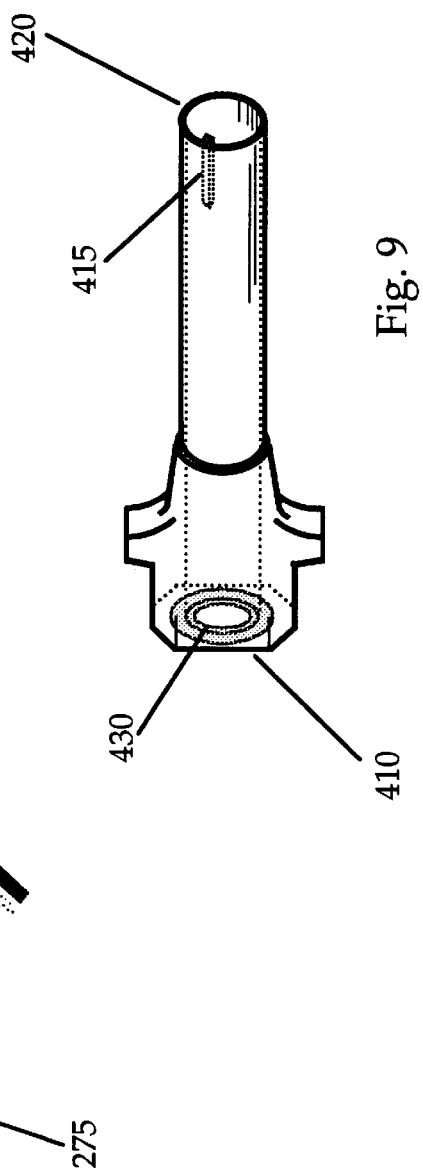

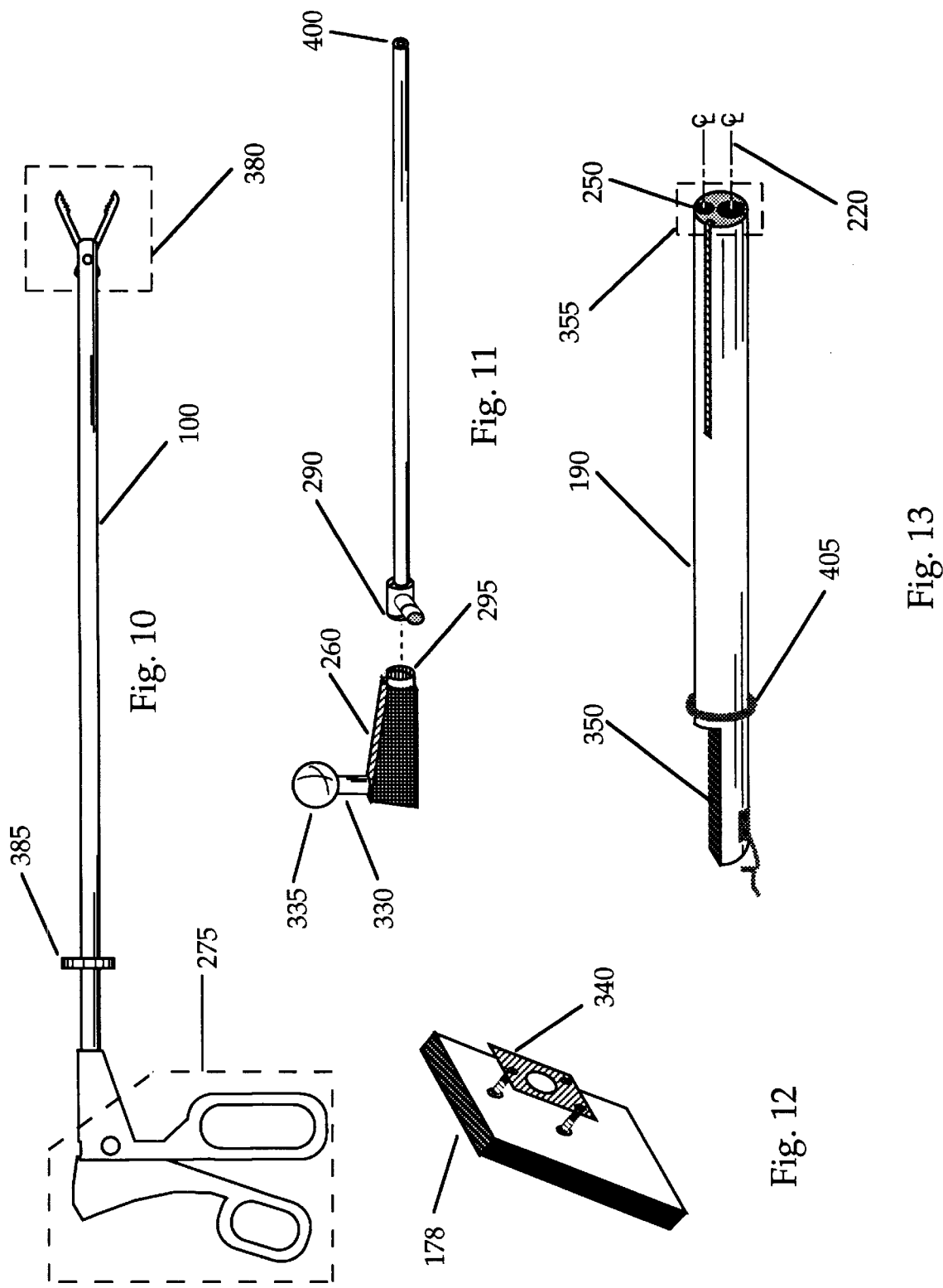

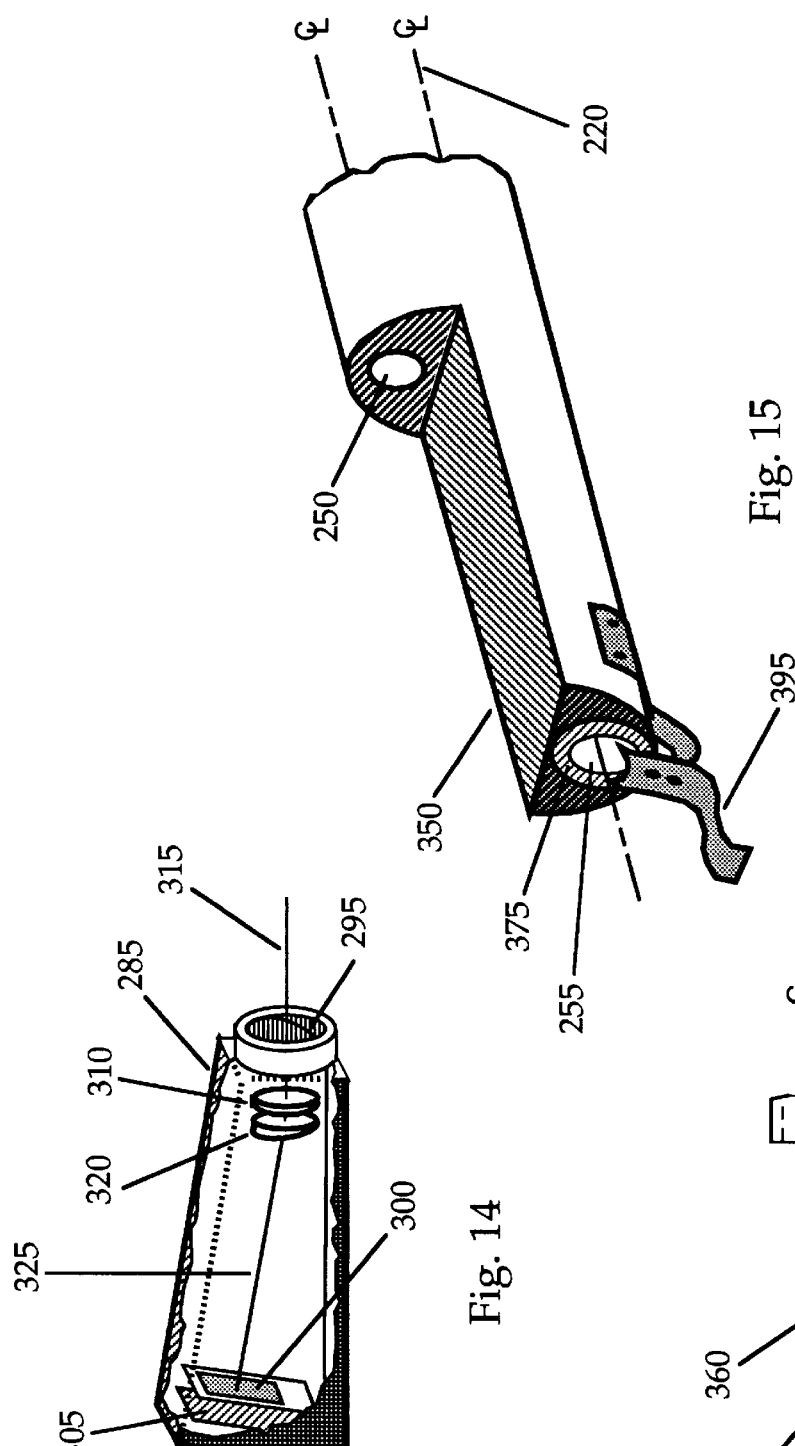
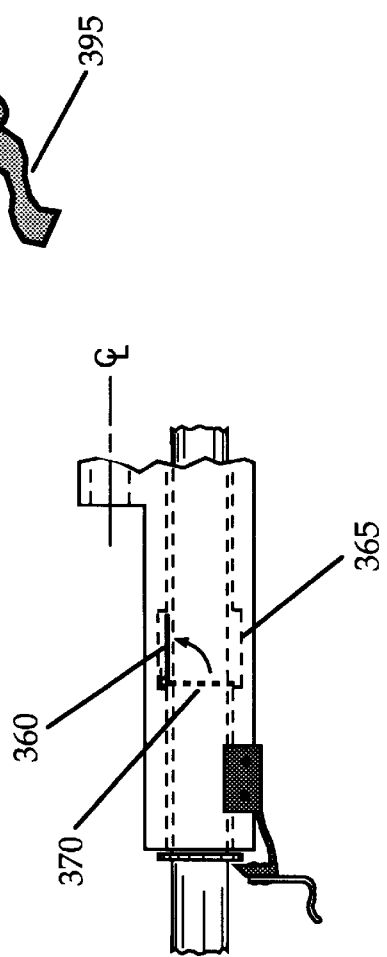
Fig. 14
Fig. 15
Fig. 16

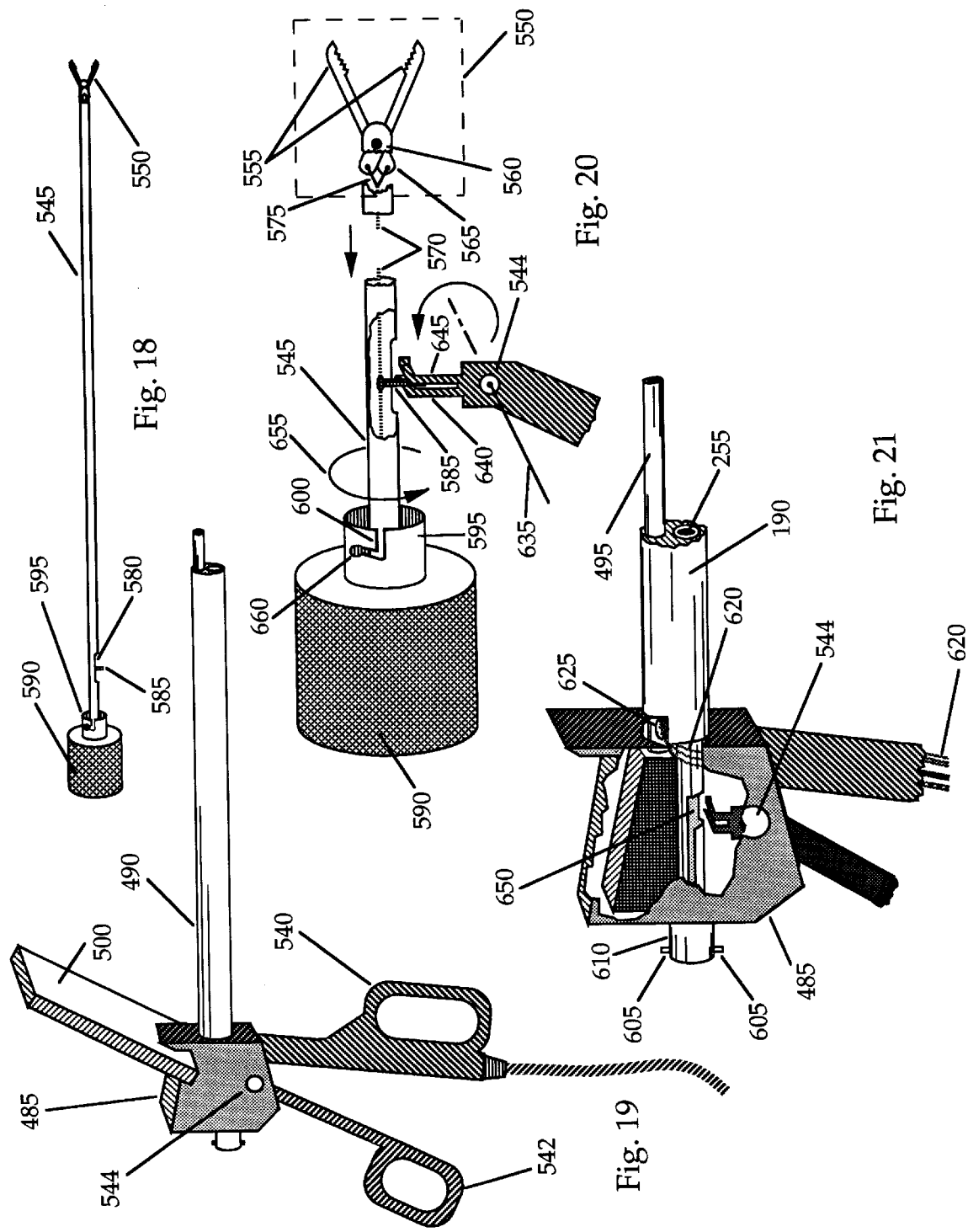

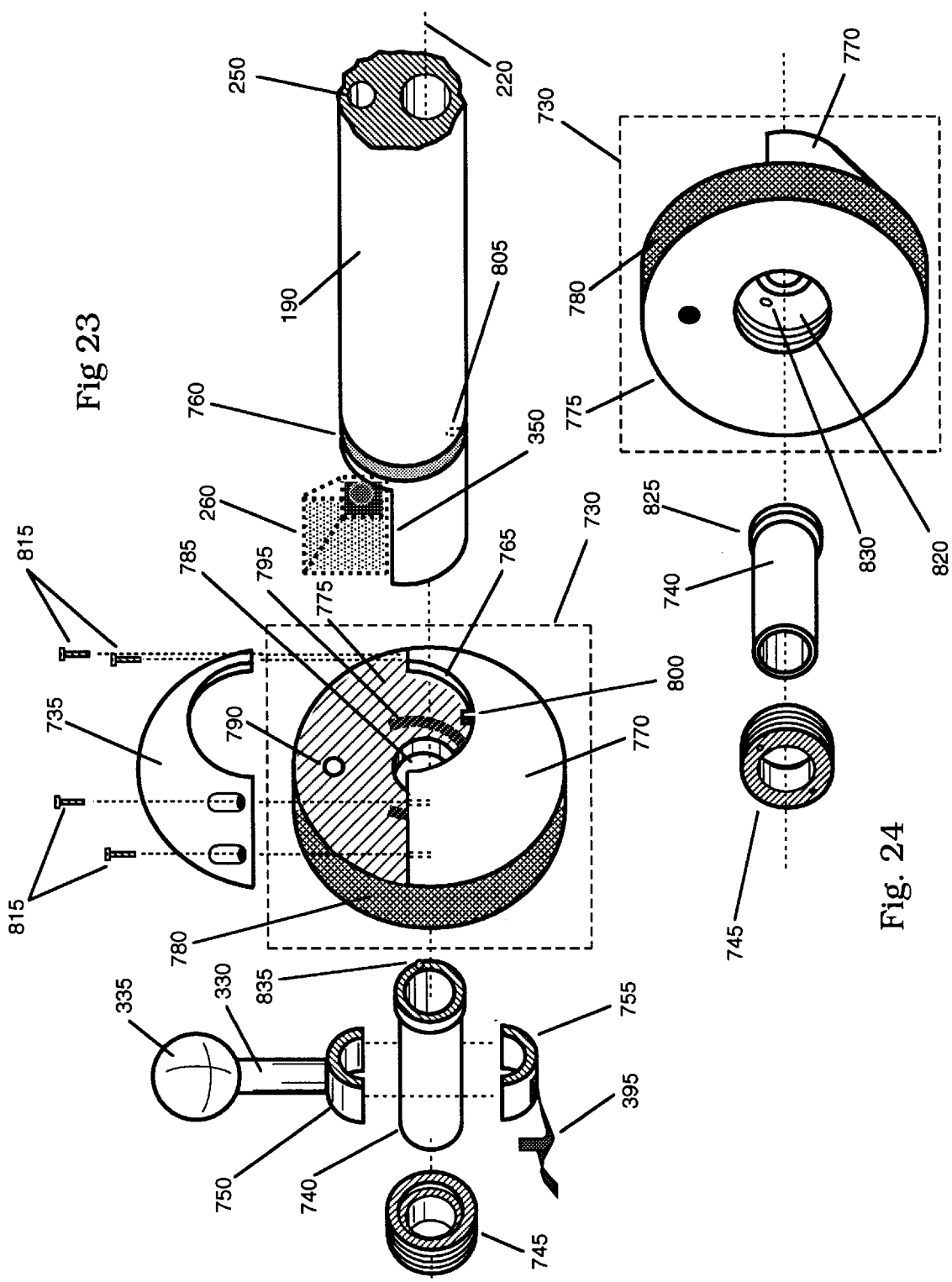

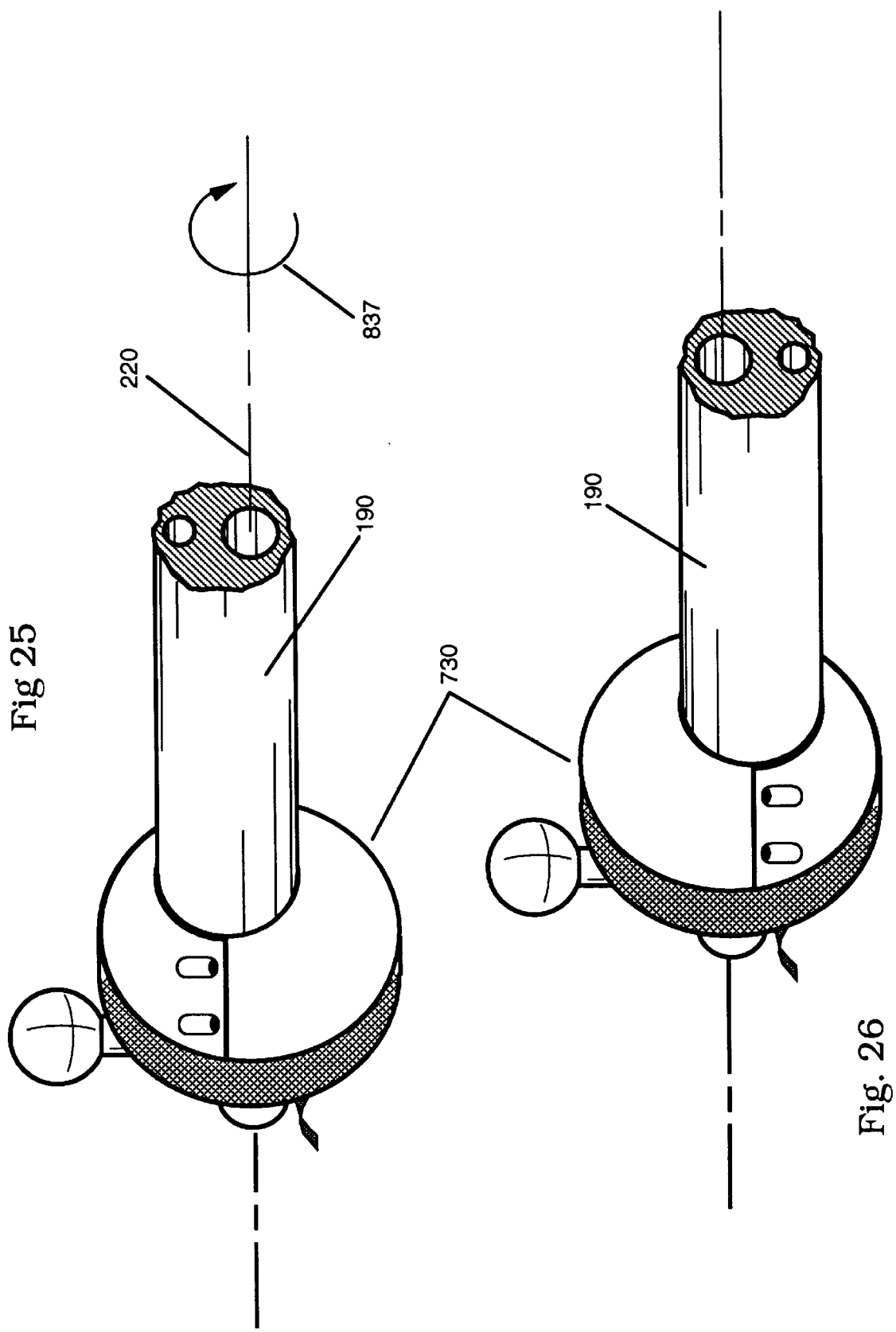

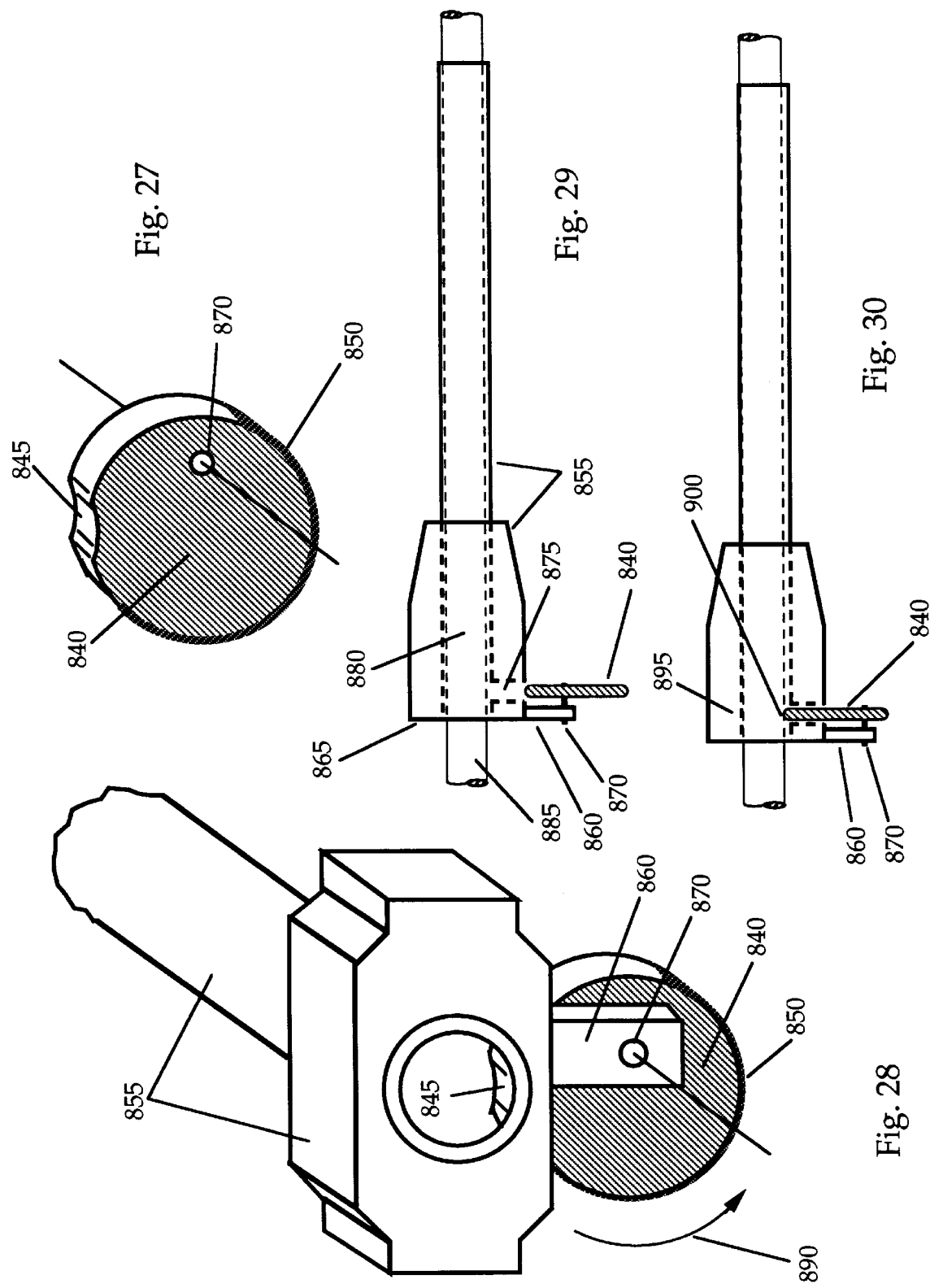

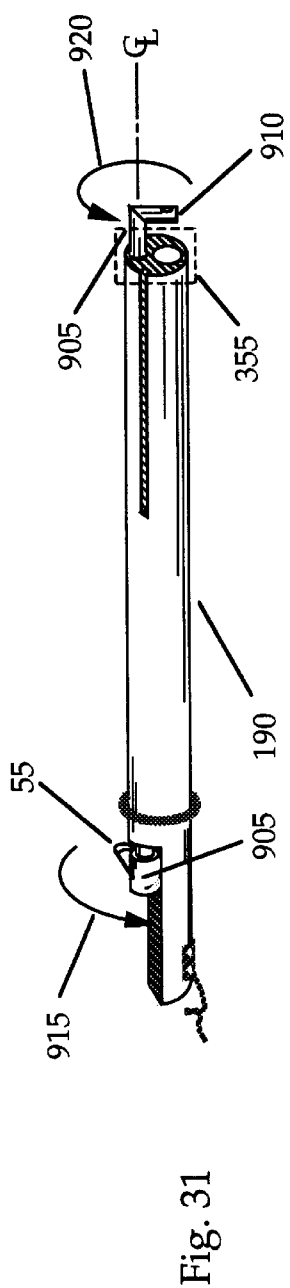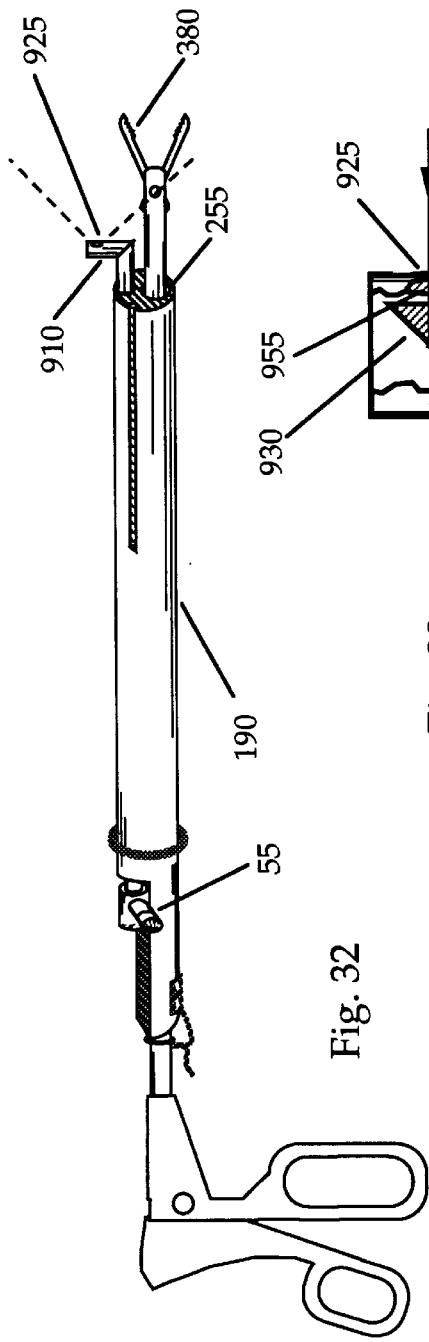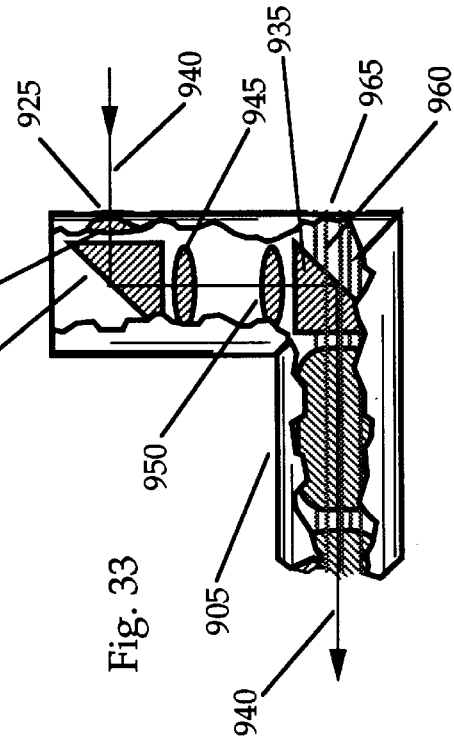

SYSTEM AND METHOD FOR ENDOSCOPIC IMAGING AND ENDOSURGERY

This application claims benefit of provisional application 60/016,830 filed May 3, 1996 also 60/021,559 filed Jul. 11, 1996.

BACKGROUND OF THE INVENTION

This invention relates to video endoscopy and to endosurgery, wherein endoscopy is understood to refer to all forms of medical endoscopy, including but not limited to laparoscopy, thoracoscopy, arthroscopy, gastroscopy, hysteroscopy, colonoscopy, and bronchoscopy, as well as to dental applications of endoscopy and to the use of endoscopic inspection instruments, such as borescopes, for non-medical applications, wherein video endoscopy refers to endoscopic visualization utilizing video acquisition and display of endoscopic images and wherein endosurgery refers to all surgical procedures performed under endoscopic visualization, including but not limited to tissue and organ repair, resection, implantation, and biopsy.

More specifically, this invention is related to a method and apparatus for improving manual dexterity in endoscopy and endosurgery by combining endoscopic, manipulative, video image forming, and video image display means in a novel manner that provides the surgeon or operator with improved hand-eye coordination.

The advantages of diagnosis and therapy performed under endoscopic visualization are well known. Such procedures are minimally invasive, result in shortened hospital stays, more rapid recovery, less cosmetic damage, and lower overall costs compared to conventional "open" procedures. However, most surgeons have much greater difficulty performing common surgical maneuvers using endosurgical instruments (long-shafted graspers, scissors, etc. commonly used in endoscopic surgery) under endoscopic visualization. Whether the image is viewed by the surgeon with his eye to the eyepiece or, as is increasingly common, on a video monitor, the surgeon has poor hand-eye coordination compared to that of open surgery. The surgeon moves the instruments hesitantly and often inaccurately, whereas in open surgery the motion is rapid and precise. Simple routines, such as suturing and knot tying, are tedious and time consuming, even for highly skilled endoscopic surgeons. As a result, endoscopic procedures generally take more operating-room time than their open counterparts and are more exhausting for the surgeon. Moreover, many capable surgeons can not adequately master endoscopic technique; consequently, surgeries that potentially could be done endoscopically are still being performed as open procedures. In laparoscopic surgery, surgeons that operate with an instrument in each hand require the assistance of another surgeon to hold and direct the laparoscope, which increases the cost of the procedure. There is a need for new endoscopic surgery instruments and methods to overcome these limitations. The present invention addresses this need. It improves on prior-art endoscopic methods by providing the surgeon with greater hand-eye coordination by making endoscopic surgery look and feel more like open surgery.

In the discourse that follows, reference is made to "enhanced presence", which is defined below in connection with a special arrangement of a video endoscope, image display, and endosurgical instrument whereby the image of the distal tip of the endosurgical instrument is presented on a video display adjacent to the instrument handle and in a specific manner, along with the bodily tissues near the tip. The intent is to induce the surgeon to act as if the image of the tip, as seen in the display, is the tip itself. The reader will understand that the surgeon will not be actually deceived in this regard, but will, nevertheless, find it natural to respond as if he were. The surgeon will thus be led to instinctively use hand motions that are effective to accomplish endosurgical tasks, whereas with conventional endosurgical apparatus these motions are difficult to learn.

SUMMARY OF THE INVENTION

In one preferred embodiment, an endoscopic visualization method according to the present invention comprises the steps of (a) inserting a video endoscope into the body of a patient and directing it to a region of interest, (b) obtaining a video image from said endoscope by means of a video camera attached thereto, and (c) displaying said video image on a video display co-located with and attached to said video camera or endoscope and viewable by the operator.

In accordance with another aspect of the present invention, an endoscopic visualization and surgery method comprises the steps of (a) inserting a video endoscope into the body of a patient and directing it to a region of interest, (b) inserting an endosurgical instrument into the body such that its distal end is within said region of interest, (c) obtaining a video image from said endoscope, and (d) displaying said video image on a video display co-located with or attached to said endosurgical instrument and viewable by the operator.

In accordance with another aspect of the present invention, an endoscopic visualization system comprising (a) an endoscope suitable for viewing the interior of a body, (b) video image detection means attached thereto, (c) video image display means co-located with said endoscope and viewable by the operator, (d) signal processing means for processing the detected images for presentation on the display means, and (e) illumination means.

In accordance with another aspect of the present invention, a system for endoscopic visualization and surgery wherein an endoscope with attached video camera or camera head and a video display are coupled with an endosurgical instrument such that the endoscope and instrument are substantially parallel to each other and in close proximity with the distal tip of instrument in the field of view of the endoscope.

In accordance with another aspect of the present invention, a system for endoscopic visualization and surgery wherein an endoscope with attached video camera or camera head and display are coupled with an endosurgical instrument such that the endoscope and instrument are substantially parallel to each other and in close proximity with the distal tip of instrument in the field of view of the endoscope.

The system for endoscopic visualization and surgery described immediately above, wherein (a) the endoscope and instrument are housed in an insertion tube, with the instrument below the endoscope (b) the display is attached to the endoscope, or to the video camera, or to the insertion tube and is located adjacent to and above the instrument's handle or hand-operated control means, so that the operator's visual perception is that the distal operative end of the endosurgical instrument, as seen in the display, is co-located with said handle or hand control means rather than at the end of a long shaft and that it is operating on tissues within a worksite located at or proximal to the display screen, which perception facilitates endoscopic surgery by providing enhanced presence.

The system for endoscopic visualization and surgery described immediately above with the exception that, in (a), the endoscope and video camera are rotated about the instrument axis to a position beneath said instrument, thereby inverting the image of the tissues within the field of view. Said configuration, when used for surgery through a port in the body surface, causes pivotal motions of the instrument about the point of entry to be reversed in the endoscopic image display, so as to more closely correspond to those of open surgery.

In accordance with another aspect of the present invention, an endoscopic visualization and surgery system comprising (a) a body piece, (b) an insertion tube affixed to the body piece, for passage into a body part, (c) an endoscope contained within the insertion tube, (d) a video camera head affixed to the endoscope, (e) a video display means affixed to the body piece or camera head, (f) electronic circuits for processing the video signals from the camera head for presentation on the display, (g) an illumination source connected to the endoscope, (h) hand control means affixed to the body piece and operably connected to instrument actuation means therein, said hand control means located below and behind the video display means, and (i) an interchangeable endosurgical instrument which, when inserted through the body piece and the insertion tube operably engages the actuation means, the distal end of said instrument projecting beyond the distal face of the insertion tube to a point beyond the distal face of the endoscope, which system improves dexterity and hand-eye coordination during endoscopic surgery by providing enhanced presence.

In accordance with another aspect of the present invention, an endoscopic visualization and surgery system wherein means are provided to rotate the endoscope position about the instrument axis so that it may be either above or below said axis, correspondingly for reverse or direct movement of the object-field image in response to pivotal movement of the instrument handle.

In accordance with another aspect of the present invention, a means for releasably locking the position of an instrument within a cannula.

In accordance with another aspect of the present invention, a periscopic endoscope and a method for its use in conjunction with an endosurgical instrument housed within an insertion tube, wherein the shaft of the endoscope is housed within said insertion tube and is first rotationally positioned such that the periscopic portion of said endoscope is within the projected area of the insertion tube, to facilitate insertion of the tube into the body, and may thereafter be rotated to an extended position, to provide a better view of the distal tip of the instrument.

In accordance with another aspect of the present invention, a method of endoscopic surgery wherein the surgeon (a) inserts a cylindrical body through a cannula in the patient, said body housing a video endoscope therewithin, (b) inserts an endosurgical instrument through said cylindrical body, such that the instrument tip is in the field of view of the endoscope, (c) maneuvers the instrument in the normal manner to conduct surgery, thereby causing the endoscope to track the movement of the instrument tip, keeping it in view, and (d) observes said video image on a monitor.

In accordance with another aspect of the present invention, a method of endoscopic surgery wherein the surgeon (a) inserts a cylindrical body through a cannula in the patient, said body housing a video endoscope therewithin and being provided with a video display affixed near the point of entry of the instrument, (b) inserts an endosurgical instrument through said cylindrical body, such that the instrument tip is in the field of view of the endoscope, (c) maneuvers the instrument in the normal manner to conduct surgery, thereby causing the endoscope to track the movement of the instrument tip, keeping it in view, and (d) observes said video image on the video display.

BRIEF DESCRIPTION OF THE DRAWINGS

FIG. 8 is a perspective drawing of the endoscopic surgery system depicted in FIG. 6.

FIG. 9 is a partial perspective drawing of a cannula for use with the endoscopic surgical system of FIG. 8.

FIG. 10 is a drawing of an endosurgical instrument such as is used in laparoscopic surgery, modified for use with the endoscopic surgery system depicted in FIG. 8.

FIG. 11 is a perspective drawing of an endoscopic telescope and a video camera head with partial mounting means for a video display, which are combined for use in the endoscopic surgery system depicted in FIG. 8.

FIG. 12 is a perspective drawing of a flat panel video display and partial mounting means for use in the endoscopic surgery system depicted in FIG. 8.

FIG. 13 is a perspective drawing of an insertion tube which is combined with the endoscope, camera head, and display for use in the endoscopic surgery system depicted in FIG. 8.

FIG. 14 is a perspective, cut-away detail drawing of the video camera head of FIG. 11.

FIG. 15 is a perspective detail drawing of a portion of the insertion tube of FIG. 13, showing the instrument retainer clip and the instrument bore seal.

FIG. 16 is a side view of the proximal end of the insertion tube showing the instrument retainer clip and the flapper valve.

FIG. 18 is a perspective drawing of an endosurgical instrument for use with the endoscopic surgery system of FIG. 17.

FIG. 19 is a perspective drawing of the basic assembly of the endoscopic surgery system of FIG. 17.

FIG. 20 is a perspective, cut-away detail drawing of the endosurgical instrument of FIG. 18 and the actuation means for operating said instrument.

FIG. 21 is a perspective, cut-away detail drawing of a portion of the basic assembly of FIG. 19.

FIG. 23 is an exploded, perspective, distal-end view of a system for switching the endoscopic surgery system between the configurations of FIG. 8 and FIG. 22.

FIG. 24 is a partial, exploded, perspective view of the system of FIG. 23, as seen from the proximal end.

FIG. 25 is an assembled view of the part of the system of FIG. 23, with the endoscope bore positioned above the instrument bore.

FIG. 26 is a partial assembled view of part of the system of FIG. 23, with the endoscope bore positioned below the instrument bore.

FIG. 27 is a perspective view of a thumb-wheel cam for use in a medical cannula.

FIG. 28 is a perspective view of the distal end of a medical cannula incorporating the thumb-wheel cam of FIG. 27, which enables releasably locking in place an instrument inserted in the cannula.

FIG. 29 is a is a side view of the medical cannula of FIG. 28 with an instrument shaft within the cannula, showing the thumb-wheel cam in a disengaged position.

FIG. 30 is a is a side view of the medical cannula of FIG. 28 with an instrument shaft within the cannula, showing the thumb-wheel cam in the engaged position, pressing the shaft of the instrument against the opposite wall of the bore of the cannula.

FIG. 31 is a perspective view of the insertion tube of FIG. 8, wherein is housed an endoscope having a periscopic distal end.

FIG. 32 shows the insertion tube and endoscope of FIG. 31, with the endoscope rotated 180° from its orientation in FIG. 31, so as to provided an elevated perspective of the tip of a surgical instrument inserted through its bore within the insertion tube.

FIG. 33 is a cut-away view of the periscopic distal end of the endoscope of FIGS. 31 and 32, showing prisms and lenses that redirect the optical path and focus the image from the entrance pupil to the endoscope axis.

DESCRIPTION OF THE INVENTION

Figure 1:
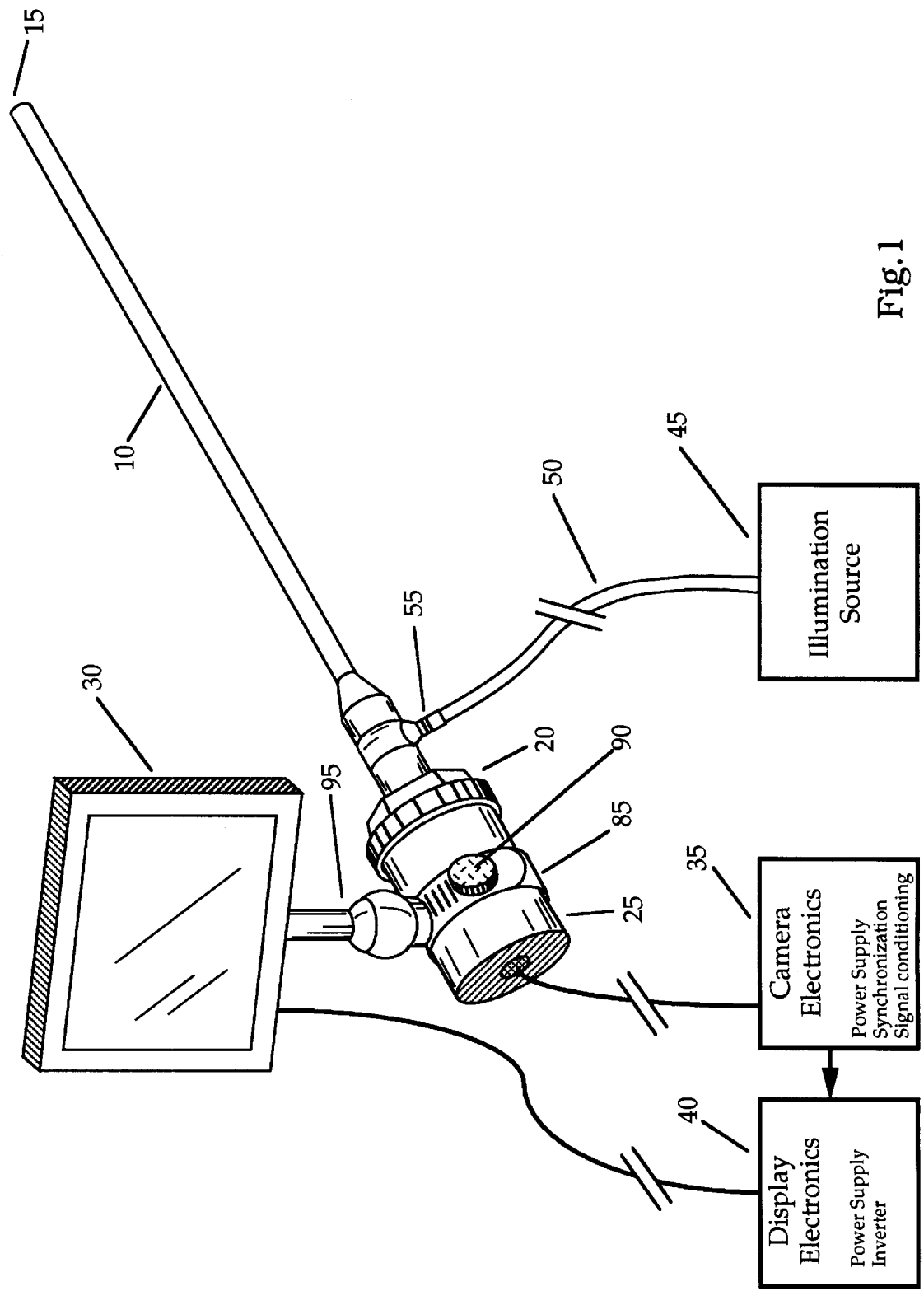
FIG. 1 is a perspective and schematic drawing of an endoscopic viewing system comprising a video endoscope with video display means releasably attached thereto, video signal processing means, and illumination means.

FIG. 1 shows a video endoscope comprising an elongated cylindrical tube 10 containing optical components that relay the images of the worksite from the distal end 15 of the endoscope to the eyepiece 20, and a video camera head 25, affixed to said eyepiece, which provides video signals corresponding to the endoscopic images. In current endoscopic practice, the video image is usually displayed on a large, cathode-ray-tube monitor, one to two meters from the endoscopist. According to the present invention, the image is presented on a video display means 30, such as a flat panel display, which, in this embodiment, is releasably attached to the camera head. The camera electronics unit 35 and display electronics unit 40 provide signal conditioning and synchronization and supply electrical power. An illumination source 45 provides light, which is conducted through a fiber-optic cable 50 to the endoscope's optical connector 55.

Figure 2:
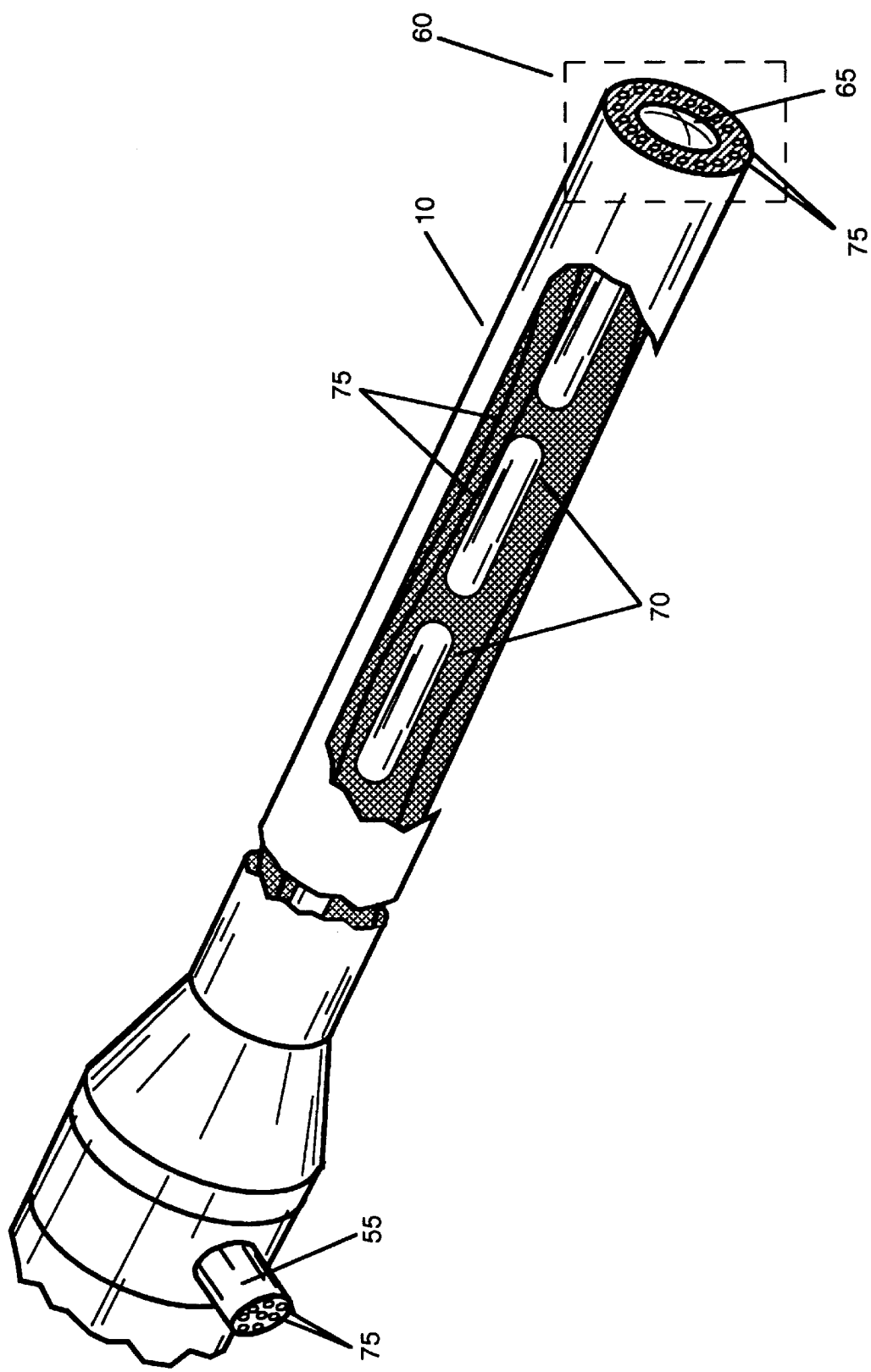
FIG. 2 is a cut-away perspective drawing of the distal portion of the FIG. 1 endoscope, showing the imaging rod lenses and the optical fibers that conduct the illumination from the optical connector to the distal face of the instrument.

FIG. 2 is a cut-away view of a portion of the endoscope of FIG. 1, including the elongated cylindrical tube 10, the distal face 60, the objective lens 65, the internal rod lenses 70, which conduct the image field from the objective lens to the eyepiece, and a plurality of optical fibers 75, which conduct light from the optical connector 55 and which terminate on the endoscope's distal face, from which said light radiates to illuminate the worksite. An example of such an endoscope is the Model 004378-901 laparoscope, manufactured by Cabot Medical Corp of Langhome, Pa. With reference again to FIG. 1, the light is supplied from the illumination source 45 to the optical connector 55 by means of the fiber-optic cable 50, which consists of a plurality of optical fibers within a flexible jacket. Endoscopic light source components suitable for this use are available, for example, from Circon-ACMI Inc. of Stamfort, Conn., as the model MV9082 Light Source and model MV8232 Fiber Light Guide, a fiber-optic cable with attached connector. Optical connectors of various designs are used by different manufacturers, and optical cables supplied with light sources generally are available with adapters to match the most commonly used endoscopes. Detachably affixed to the eyepiece 20 is a video camera head 25, which comprises a charge-coupled device (CCD) imaging array, a lens system, and a preamplifier, which is connected to the camera electronics unit 35, which contains power supplies, synchronization and digital addressing circuits, and signal conditioning circuits. The Circon-ACMI model 9660 camera head and camera electronics unit are suitable for this application.

In addition to the video endoscope system described above, video endoscopes of other designs also may be used in this invention, such as those with coherent optical fiber bundles instead of rod lenses, as described by Dorsey and Tabbs, with solid state image detectors located at their distal end, such as the model EVG-F from Fujinon, Inc., Scarsdale, N.Y., and with flexible rather than rigid, i.e., inflexible, tubes, e.g., the model P20 from Olympus Optical Company. Rigid endoscopes are endoscopes that can not be substantially deformed without damage to their internal optical elements. Flexible endoscopes include endoscopes with slightly bendable optics and thin metal walls, which are used in some arthroscopic procedures, and highly flexible endoscopes for the digestive tract and bronchi, which have soft plastic jackets. For medical use, these endoscopes are made in different sizes and shapes for a wide variety of diagnostic uses and for image-guided minimal-access surgery.

Referring again to FIG. 1., a video display means 30 is affixed to the endoscope, eyepiece, or camera head by a releasable mounting means, which permits the removal of the display means from the endoscope. The illustrated mounting means comprises a strap 85 of adjustable length and an adjustment knob 90 with which the strap can be shortened until it firmly grips the camera head. Conversely, the knob may be used to loosen the strap, enabling removal of the display. Detachability of the display may be desirable in medical endoscopy as it enables the endoscope to be autoclaved without damage to the display means, which may not endure high temperatures. The images produced by the video camera are viewed on the display means, enabling the endoscopist to see the image while directing his visual attention to the physical placement of the endoscope. The display 30 is adjustably attached to the mounting means by a ball and socket 95, with which the endoscopist may reposition the display for optimum viewing.

The display means 30 indicated in FIG. 1 preferably has a diagonal screen measurement of 70 mm to 120 mm, but may be any size that is convenient, and is light weight, for example, less than 50 gram. Although any video display may be used, a flat panel display (FPD) has certain weight and size advantages. By flat panel display is meant any means of video display that is thin compared to height and width and is light-weight compared to a conventional cathode-ray tube display. Flat panel displays include but are not limited to liquid crystal displays (LCD), field emission displays (FED), plasma displays (PD), and electroluminescent displays (ED).

The display may be entirely self contained, i.e., including within its housing all electronic circuits required to convert any standard video signal into a picture. It may even include batteries, such as does the Citizen model M329, available from CBM America Corp of Santa Monica, Calif. Alternatively, to reduce its size and weight, it may employ an external power supply and power inverter, situated in an external signal processing unit such as the display electronics unit 40 of FIG. 1. The Model LQ4NC01/02, manufactured by Sharp Electronics Corp., of Camas, Wash. is suitable for use in this manner.

Figure 3:
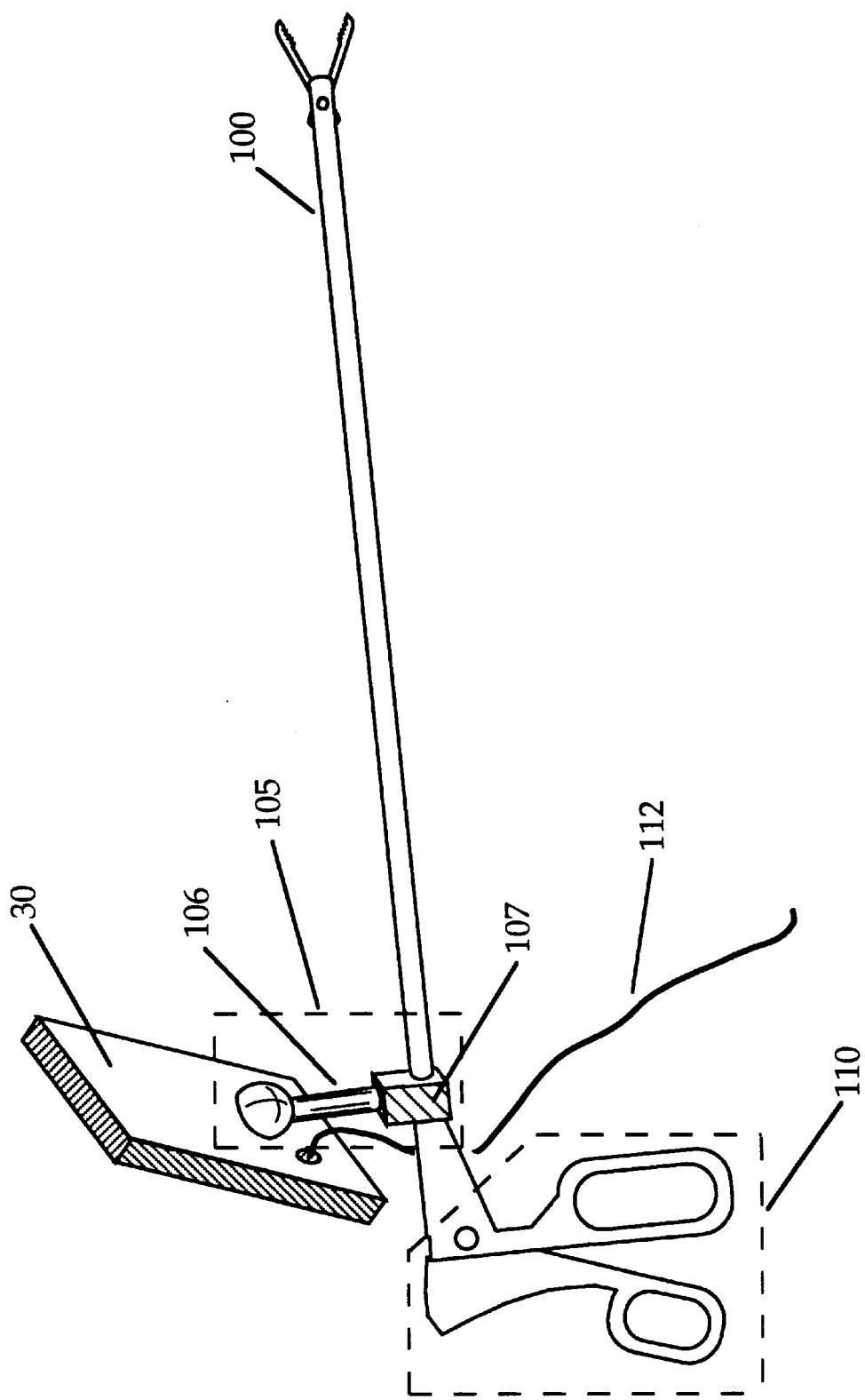
FIG. 3 is a perspective drawing of an endoscopic surgical instrument in combination with a video display means.
Figure 4:
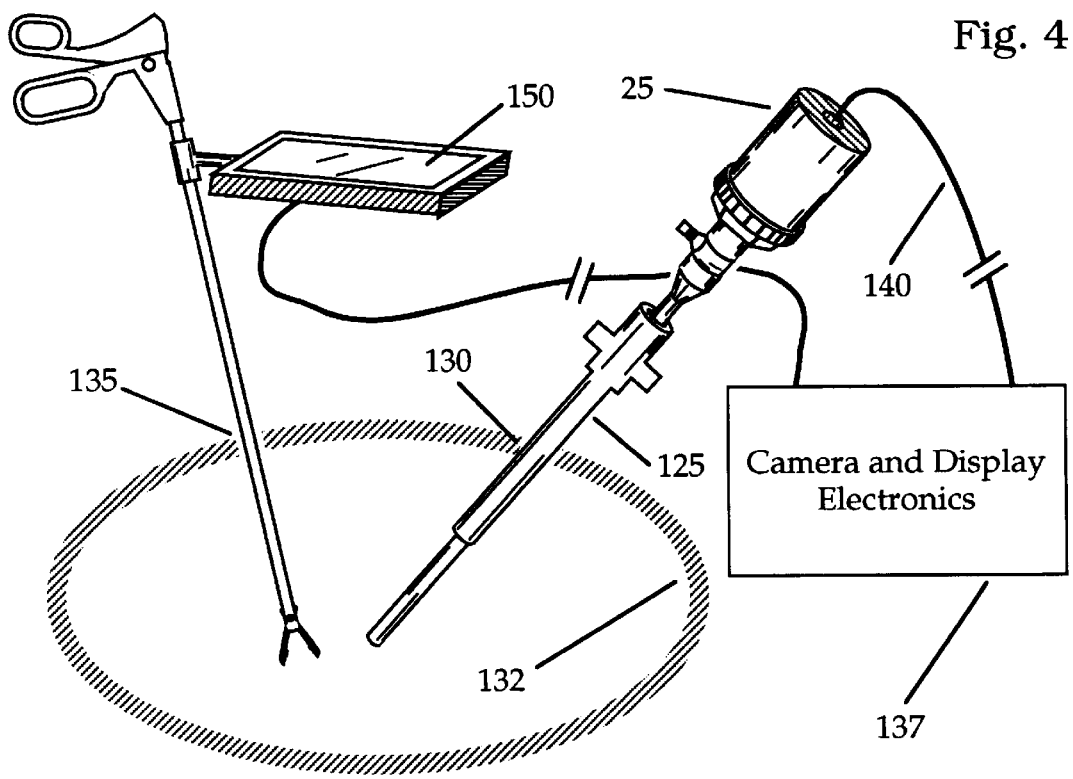
FIG. 4 is a perspective drawing and diagram of a system and method for endoscopic examination and surgery within a body, utilizing a video endoscope, an endoscopic surgical instrument separately disposed therewithin, and a display means attached to said instrument, wherein the displayed image is derived from said video endoscope.

FIG. 3 shows an alternative embodiment of the present invention wherein a video display means 30 such as a flat panel display is affixed to an endoscopic surgical instrument with elongated shaft 100 with a mounting means 105 near its handle or hand-operated control means 110, enabling the surgeon to see the displayed image while directing his view toward the patient, his hand, and the instrument. The mounting means comprises a support stem 106 affixed to the back of the display, which is affixed to the top of a polymer or hard rubber block 107, through which the endosurgical instrument is passed, forming a releasable friction grip that holds the display in the selected position. Both instrument and display are adjustably secured by friction in their respective holes in the block. Video signals and electrical power to operate the display are supplied to the display through a cable 112, from electronic units, as described with reference to FIG. 1. Examples of endoscopic surgical instruments suitable for use in this embodiment are 5-mm-diameter laparoscopic instruments such as the Endo Grasp graspers, Endo Shears scissors, Endo Bowel damps, and Endo Clip clip-appliers, which are manufactured by United States Surgical Corp. of Norwalk, Conn. With reference to FIG. 4, the image on the video display 150 is generated by a separate endoscope 120. The separate endoscope may be a conventional 10-mm diameter laparoscope such as is described above. The endoscope is inserted through a conventional trocar cannula 125, such as the Surgiport, manufactured by United States Surgical Corp., which passes through a first port 130 in the external surface 132 of the body part under examination. The distal end of the endoscopic surgical instrument is inserted through a second port 135 for the purpose of surgical manipulation within the field of view of the endoscope. The video signals from the video camera head 25 are conducted to the video camera electronics unit 137 through a first electrical cable 140 and thence through a second electrical cable 145 to the video display means 30.

Figure 5:
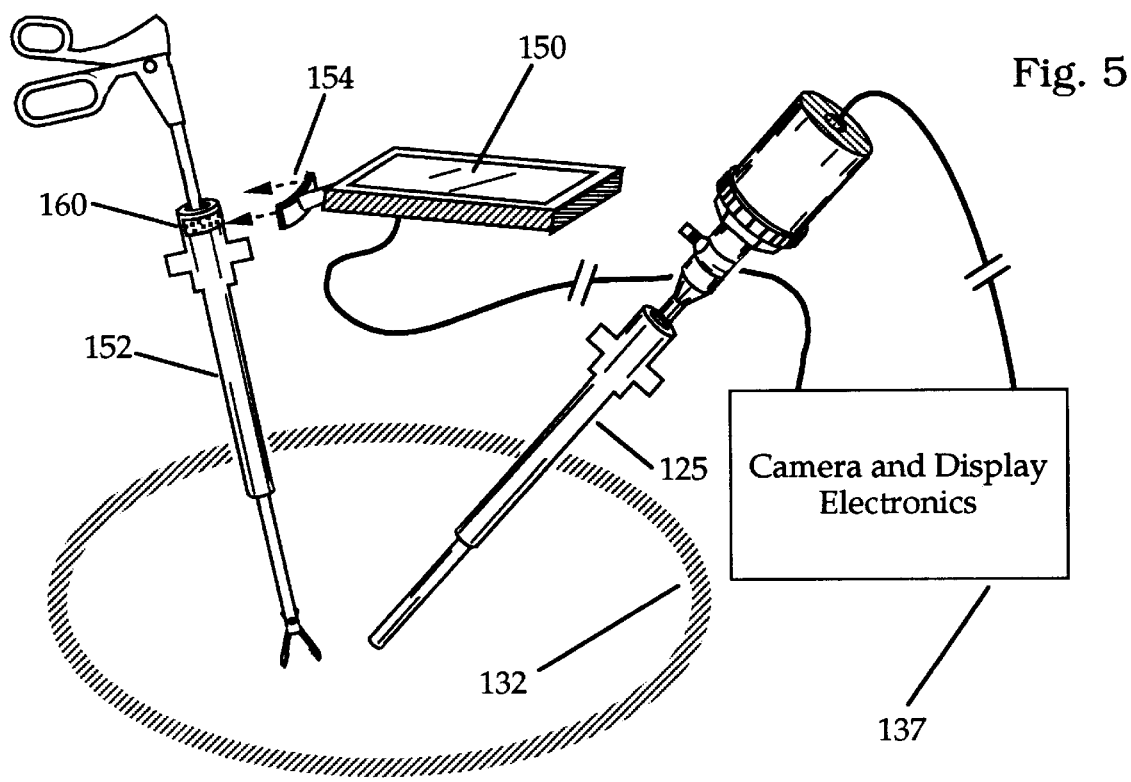
FIG. 5 shows a variation upon the system and method of FIG. 4 wherein the endoscopic instrument is introduced within the body through a cannula and the display is attached to the cannula rather than to the instrument.

FIG. 5 shows another embodiment of the present invention wherein the endoscopic surgical instrument is inserted into the body part by passage through a cannula 152, wherein the video display 150 is releasably affixed to the cannula by a mounting means comprising a support member 154, a Velcro strip 155, adhesively bonded to the support member, and a corresponding fabric anchoring strip 160 adhesively bound to the cannula. Materials for implementing this mode of attachment are commonly available. The display will be readily dismounted from the cannula before the cannula is sterilized or discarded.

Figures 6, 7:
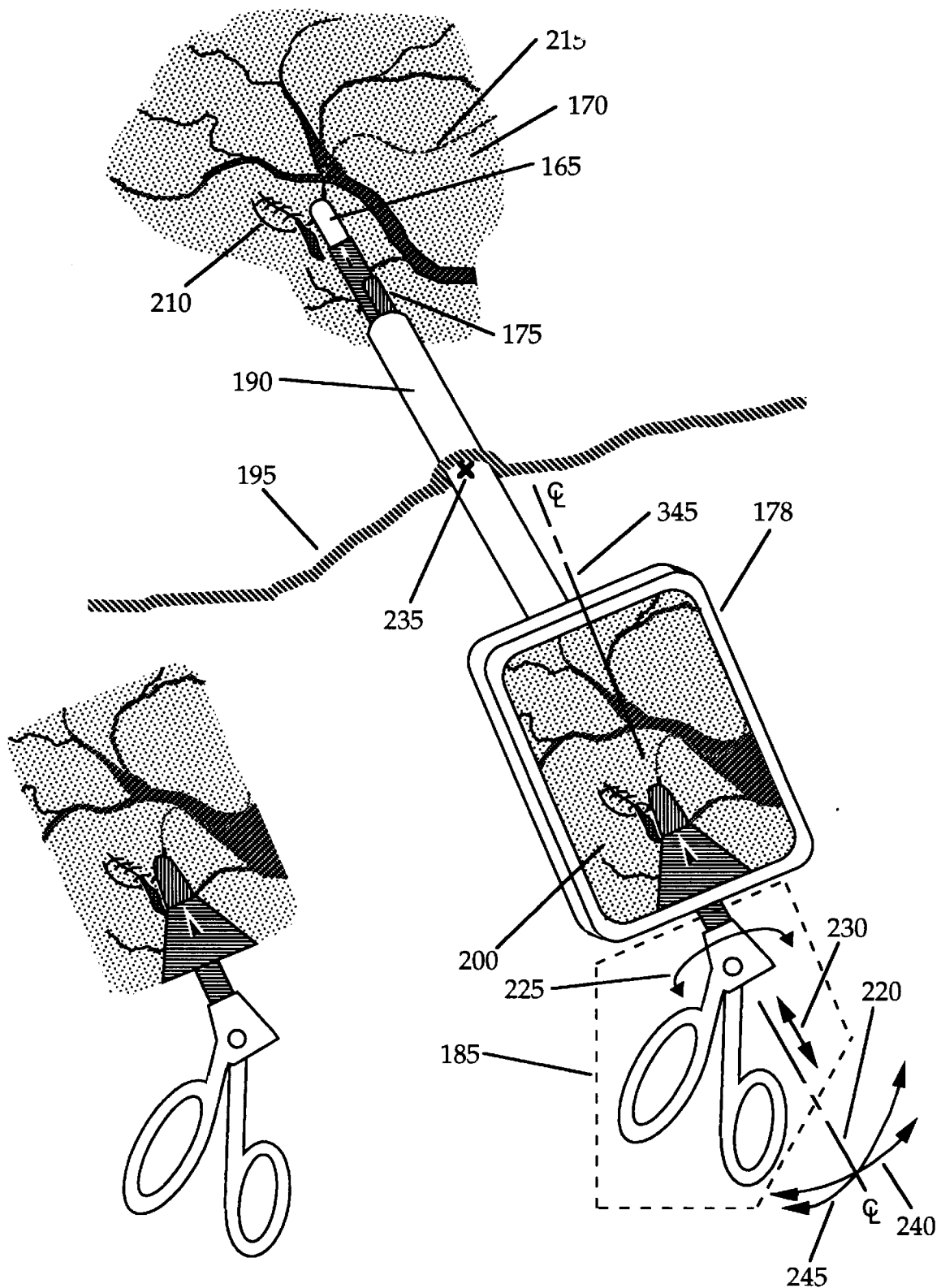
FIG. 6 is a perspective drawing of an endoscopic surgery embodiment of the present invention combining an endoscope, a video camera, a video display means, an endoscopic surgical instrument, and an insertion tube.
FIG. 7 is a rendering of the visual illusion created through use of the FIG. 6 embodiment, whereby the distal tip of the endoscopic surgical instrument, as observed in the video image, appears to be operably attached near the instrument handle, with the internal body tissues in the plane of the display.

FIGS. 6 through 16 illustrate another embodiment of the present invention. It is directed to making endoscopic surgical manipulation faster and more accurate by bringing the apparent position of the distal tip of the endoscopic surgical instrument and operative site close to the instrument handle, as it would be in open surgery, thereby improving hand-eye coordination. With reference to FIG. 6, this is achieved by generating a video image of the endosurgical instrument's distal tip 165 and of the operative site 170 from a video endoscope adjacent to and substantially parallel to said instrument, the distal tip 175 of said endoscope lying just proximal to the instrument tip 165 and presenting the said image on a video display 178, which display is located at a point just distal to the instrument handle or hand-operated control means 185. The endoscope's tube 10 (ref. FIG. 1) and the instrument shaft 100 (ref. FIG. 3) are enclosed in an insertion tube 190, which is passed through the external surface 195 of the body part under examination. In the case of abdominal surgery, generally, a trocar cannula is first inserted through the abdominal wall and the instrument or endoscope is passed through it, as depicted in FIG. 5. Similarly, in the FIG. 6 embodiment, the insertion tube may enter the body through a cannula.

As FIG. 6 illustrates, the instrument handle is colocated with the image 200 of the instrument tip and tissues within the operative site are co-located. When looking at his hand and the instrument handle 185, the surgeon sees, in the same view, the image of the tip of the instrument, positioned as if it were extending immediately from the handle, and of the tissues and organs, which appear to be just beyond the nearby instrument tip. The surgical instrument depicted is a needle holder, such as the Szabo-Berci Needle Driver, made by Karl Storz Endoscopy, Culver City, Calif. It is shown inserting a needle 210 with attached suture 215 through the tissue 170. This perception, depicted in FIG. 7, is familiar to all surgeons from their experience with open surgery.

As will become apparent through reference to FIGS. 6 through 16 below, the orientation of the image of the instrument tip is fixed with respect to the instrument shaft, owing to the fixed relationship between the instrument, the video endoscope, and the display. Referring again to FIG. 6, rotation of the instrument about its longitudinal axis 220, as indicated by arrow 225, causes the tip image to rotate about its axis in the display by the same degree. Advancing or withdrawing the instrument, as indicated by arrow 230, does not alter the positional relationship between the handle and the image of the tip, because the instrument, insertion tube, video endoscope, and video display move in and out as a single unit, as will become evident according to FIGS. 8 and 9 Again referring to FIG. 6, angular movement of the instrument handle about the fulcrum point 235 at the point of insertion through the abdominal wall, as indicated by the arrows 240 and 245, does not alter the relationship between the handle and the image if the tip. These fulcrum-constrained motions are identical to the motions that can be made in conventional laparoscopic surgery; however, with the present invention, the surgeon will be able to make them with more spontaneity and rapidity.

Attention is now directed to FIGS. 8 through 16, wherein a preferred embodiment of the conceptualization of FIG. 6 is depicted. FIG. 8 shows an assembled surgery system, as would be used, for example, in laparoscopic surgery, with the omission of the separate camera electronics and display electronics units and the illumination source, these having been described in connection with FIG. 1. The mountable display is shown detached to indicate that the FIG. 8 embodiment can also be used without the attached display, by a surgeon viewing the image on a conventional monitor. The system comprises an insertion tube 190, an endoscope occupying a first longitudinal bore 250 in the insertion tube with its distal 175 end extending beyond the end of said tube, an endoscopic surgical instrument with its shaft 100 inserted through a second longitudinal bore 255 within the insertion tube, which bore is below the bore containing the endoscope, a video camera head 260 affixed to the proximal end 265 of the endoscope, a video display 178, a mounting assembly 270 for holding the video display in a position above the handle 275 of the instrument with adjustable orientation, an electrical cable 280 that carries power and video signals between the camera and display and the electronic processing unit, and a fiber-optic cable 50, which conducts the illumination energy from the illumination source to the optical connector 55 of the endoscope.

For purposes of maneuverability and ease of use, it is desirable to make the diameter of the insertion tube as small as is practical, consistent with the need to accommodate the endoscope and instrument. For example, an outer diameter of 10 mm or less would permit the insertion tube to pass through a standard 10-mm trocar cannula such as the 10-mm abdominal Surgiport, manufactured by United States Surgical Corp, depicted in FIG. 9 with a modification described below. It is desirable to use available endoscopic surgical instruments with shaft diameters of 5 mm. As construction materials and clearances will consume part of the remaining diameter, the available space restricts the endoscope diameter to be no more than 3 mm. Also, the endoscope must be long enough. The length of the shaft of a typical laparoscopic surgical instrument is about 330 mm. An endoscope length of 220 to 250 mm would satisfy this requirement. One endoscope with suitable dimensions is the bronchoscopic telescope Model 27018 A-C, manufactured by Karl Storz, which is 2.7 mm in diameter and 240 mm long. In this application, its eyepiece is replaced by a small video camera head coupled directly to the proximal end of the telescope portion. Referring now to FIGS. 11, 13, 14, and 15, the video camera head 260 comprises a housing 285 which is releasably coupled to the endoscope by matching threaded ends 290 and 295, a charged-coupled-device (CCD) image sensor 300, a preamplifier 305, and a lens system 310 to focus the endoscopic image on to the image sensor. Modular CCD cameras suitable for this application, comprising small image sensor/preamplifier units and separate signal processing boards, are available, such as the model YH-7B20 camera from Sharp Corporation. As the endosurgical instrument channel is only a few millimeters away from the endoscope channel, there may not be sufficient radial clearance to center the image sensor on the endoscope axis 315. Accordingly, the lens system incorporates a prismatic element 320 that redirects the optical axis 325 away from the instrument channel. Alternatively, a mirror or internally reflective prism can be used to redirect the optical axis. Optical systems such as these are readily designed with existing lens-design software and are fabricated with stock optical components or with specially fabricated components, for which there are many suppliers in the optics industry, for example, Ferson Optics in Ocean Springs, Miss.

With reference to FIGS. 11 and 12, the adjustable mounting assembly 270 (ref. FIG. 8), by which the flat panel display 178 is attached to the video camera head 260, comprises a post 330 with attached metal ball 335 and an adjustable ball-retainer 340, attached to the display, by which the ball is held with sufficient friction to prevent unintended movement of the display. The orientation of the display may be readily adjusted by the endoscopist or surgeon for optimum viewing. With reference to FIG. 8 and particularly FIG. 6, the display may be perpendicular to the insertion tube or it may be inclined, as shown, with the top of the display rotated down toward the insertion tube. This will bring the axis 346 of the image of the instrument tip into closer alignment with the axis 220 of the instrument itself, strengthen the visual illusion that the image of the tip is connected coaxially with the instrument shaft. Individual surgeons may differ as to the most effective degree of tilt. As with any two-dimensional display of a three-dimensional field, there is directional ambiguity with regard to distances and motions. Inclining the display allows each user to minimize for himself the confusion caused by this ambiguity. In an alternative configuration of this embodiment, the display 178 and mounting assembly 270 are omitted and the surgeon views the image on a separate monitor, as discussed below with respect to FIG. 34.

With reference to FIGS. 13 and 15, the insertion tube 190 comprises a housing, made, for example, of plastic, approximately 250 mm in length. At its proximal end is a recessed plateau 350 which provides clearance for the video camera head. The endoscope, with camera attached, is inserted into the first bore 250 until it extends to or beyond the distal end 355 of the insertion tube by between 0 and 20 mm; it is secured therein by friction between the shaft and bore. The endoscope, camera head, and display may be removed from the insertion tube after use, so that they may be cleaned separately.

With reference to FIGS. 15 and 16, to limit the loss of insufflation gas when no instrument is in the instrument bore of the insertion tube, a flapper valve 360 (shown open) is provided within an enlarged portion 365 of the second bore 255. Such valves are in common use for the same purpose in trocar cannulas made by U.S. Surgical Corp. (referenced above.) Insertion of the instrument causes this valve to rotate up from its closed position 370 to its open position, as shown, clearing the bore for passage of the instrument. To limit the loss of insufflation gas during use of an instrument, a wiper seal 375 is provided at the proximal end of the instrument bore, comprising a flexible membrane with a hole slightly smaller than 5 mm. Such membrane seals are in common use for the same purpose in trocar cannulas made by U.S. Surgical Corp. (referenced above.)

With reference to FIG. 10, the instruments used in this embodiment are standard 5-mm laparoscopic surgery instruments, either resuable or disposable, such as the "Endo" series manufactured by United States Surgical Corp.

and previously referenced herein. They comprise a hand-operated control means 275, a long hollow shaft 100, and end effector 380, and internal actuation means through which the hand-operated control means actuates the end effector. In the present invention these instruments are modified by the addition of a retainer ring 385, which is positioned and compressed to secure it around the shaft prior to use. With reference to FIGS. 8, 13, and 15, the purpose of the retainer ring is to ensure that during operation the instrument remains in the desired position along the instrument axis 220 with respect to the insertion tube. With reference to FIGS. 13, 15, and 16, the instrument is releasably locked in place by a spring-metal-mounted retaining latch 395 which engages retainer ring 385. When thus engaged, the distal tip of the end effector 380 of the instrument extends beyond the distal end 400 of the endoscope by a preselected distance, which is generally between 20 and 50 mm. Thereby, if the endoscope is of the "straight-ahead" type, i.e., the field of view is symetrically disposed about the endoscope axis, then the instrument tip generally will occupy the central portion of the lower third of the endoscope's field of view, as depicted in FIG. 6. Once the latch is engaged, the instrument cannot move in or out, but it is free to rotate about its axis. The instrument may be released by a downward deflection of the retaining latch. It may then exchanged for another instrument without removing the insertion tube from the cannula.

In response to inward or outward force on the instrument handle, the insertion tube advances or withdraws within the cannula. With reference to FIGS. 8 and 9, the extent to which the insertion tube may be advanced is limited by the stop ring 405, which comes to rest against the proximal end 410 of the cannula at the point of greatest insertion. It is preferred that torque applied to the instrument handle to rotate the instrument about its axis does not induce rotation of the insertion tube within the cannula, as this would cause the display to rotate (it should be noted, however, that, because the endoscope and display would undergo the same rotation, the image of the tissues would not change in orientation.) With reference to FIGS. 8, 9 and 13, to ensure that the insertion tube does not rotate with respect to the cannula, a raised bar 415 is incorporated on the inside surface of the distal end 420 of the cannula and a mating grove 425 is made on the outside of the anterior portion the insertion tube, so that the grove and bar must be aligned for the distal end of the insertion tube to pass through the distal portion of the cannula. When grove and bar are engaged, the insertion tube is free to move in and out of the cannula but no relative rotation of the insertion tube and cannula is possible. The grove does not extend to the anterior portion of the insertion tube surface as this would interfere with the integrity of the contact between said surface and the round wiper seal 430 at the proximal end of the cannula, resulting in a leakage of insuflation gas.

To utilize this invention, according to the embodiment of FIGS. 8 through 16, for endoscopic visualization and surgery, the surgeon first places the cannula into the patient using well known endosurgical methods, such as those described by Phillips, et al. Then, the insertion tube, with the endoscope, camera head, and display attached thereto, is inserted into the cannula. An endoscopic surgical instrument is selected and inserted into the instrument bore of the insertion tube, engaging the retainer latch. The distal end of the instrument is now in position to execute a surgical maneuver on the internal tissues. The endoscopic image of the distal instrument tip and the tissues are visible in the display, just above the instrument handle.

Rotation of the instrument handle about the instrument axis causes the instrument to rotate within the insertion tube. The instrument tip is seen in the display to execute a corresponding rotation. Advancing and withdrawing the instrument handle causes the insertion tube to move in and out of the cannula, thereby, the image of the instrument tip remains always in the same position on the display screen. The visual perception provided by this embodiment, as illustrated in FIG. 7, is akin to that of open surgery—a short-handled instrument operating on tissue located near the surgeon's hand. Lateral motion of the instrument tip is produced in the customary laparoscopic manner—by rotating the instrument handle about the fulcrum that is established by the cannula at the point of insertion in the body part. It is within the scope of this invention to omit the attached display, in which circumstance the surgeon views the image on a conventional monitor. Although enhanced presence would not be provided, nevertheless, the surgeon may operate with an instrument in each hand, keeping the endoscope trained on the region of interest without conscious effort and without an assistant to direct the endoscope. This is further described below with respect to FIG. 35.

Figure 17:
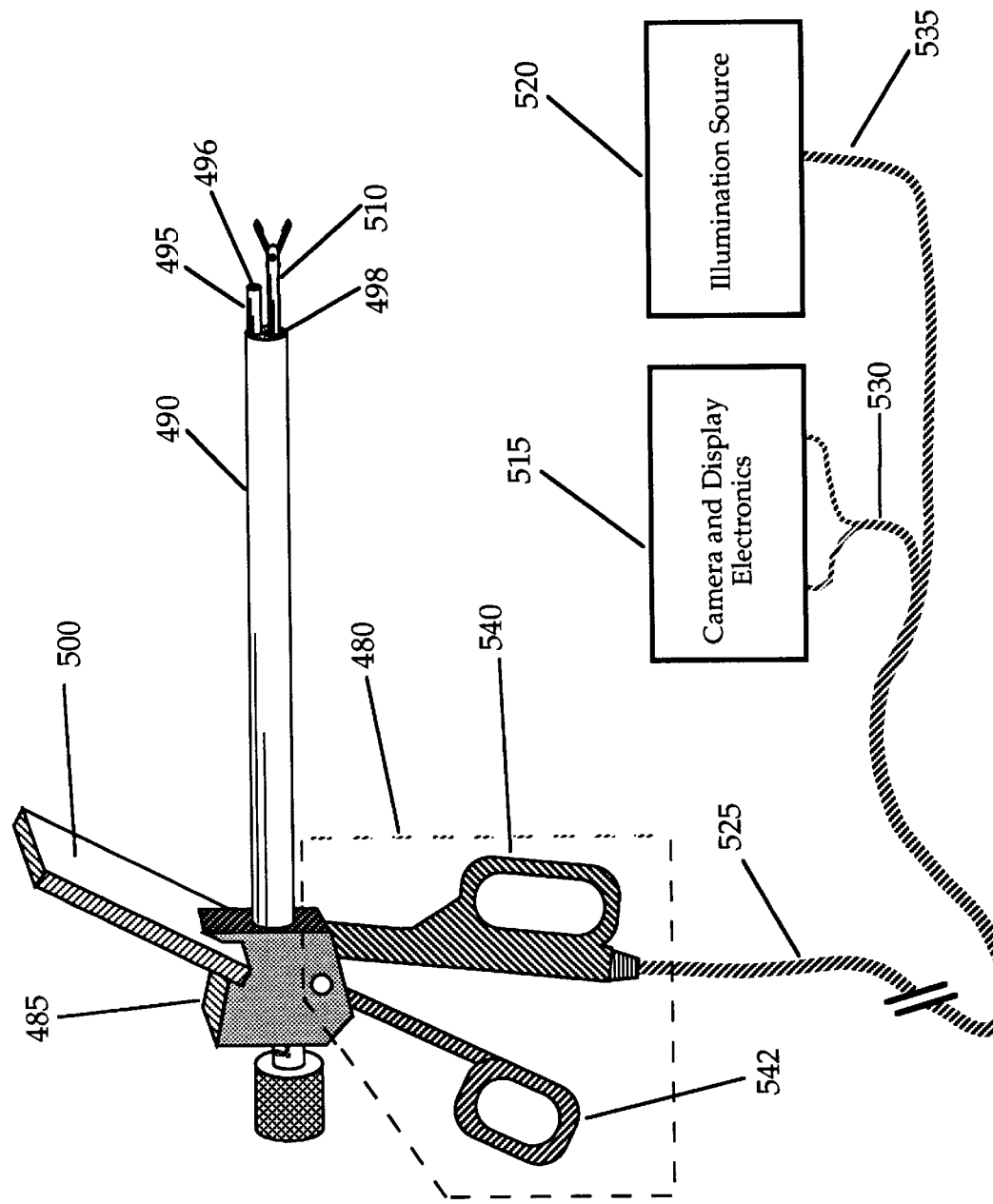
FIG. 17 is a perspective and schematic drawing of another embodiment of the present invention comprising an endoscopic surgery system wherein the hand operated controls are integrated with the insertion tube, camera, endoscope, and display, and interchangeable instruments are engaged by and operated by said controls.

Attention is now directed to FIGS. 17 through 21, which illustrate another embodiment of the present invention. With reference to FIGS. 17, 18, and 19, in this embodiment the hand-actuated controls 480 are combined with a body piece 485, insertion tube 490, endoscope 495, and display 500 to form a basic assembly, which, in combination with a compatible instrument 510, camera and display electronics unit 515, and an illumination source 520 form a complete endoscopic surgical system. In FIG. 17, the system is shown fully assembled and ready for operation, with an interchangeable instrument 510 inserted. A single cable 525, containing within it an electrical 530 and an optical 535 cable, is dressed through the forward member 540 of the hand-operated control means 480, which is affixed to the body piece 485 of the basic assembly. Said cable branches thereafter, with the electrical branch connecting to the camera and display electronics unit 515 and the optical branch connecting to illumination source 520. A rearward member 542, of the hand-operated controls 480 is pivotally mounted at pivot point 544 to the body piece 485 for the purpose of actuating the instrument, as described below.

FIGS. 18 through 21 illustrate certain details of the embodiment of FIG. 17. With reference to FIGS. 18 through 21, the interchangeable compatible instrument 510 comprises a cylindrical hollow shaft 545, an end-effector 550 (e.g., a grasper or scissors) comprising two operative elements 555 pivotally mounted to the shaft at a point 560 near the shaft's distal end, a hole 565 in each operative element proximal to the pivot point, a drive rod 570 located within the shaft and coupled to the operative elements by two short wires 575 each passing through the hole of one of the operative elements, a longitudinal slot 580 in one side of the shaft, a drive pin 585 affixed to the drive rod and extending through slot 580, a knob 590 on the proximal end of the shaft, and a twist-lock means immediately distal to the knob and concentric with the shaft 545, said twist-lock comprising a first cylinder 595 with a slot 600 on each side, said slots suitably shaped for releasably engaging opposing bayonets 605 (ref. FIG. 21) projecting outward radially from a second cylinder 610 of smaller diameter, affixed to the proximal end of the body piece, which cylinder is concentric with the instrument bore 255 in the insertion tube 190.

With reference again to FIGS. 17 through 21, the endoscope 495, with the video camera head 260 attached to it, is mounted in the basic assembly 485 such that the distal end 496 of the endoscope extends beyond the distal end 498 of the insertion tube by a distance suitable for the surgical use intended, which may be between 0 and 20 mm. The optical fibers 620 that conduct light to the endoscope for field illumination originate at the illumination source, pass through the forward member 540 of the hand-operated control means, enter the endoscope through a light-sealed aperture 625, and continue to the distal face of the endoscope, where, as illustrated in FIG. 2, they terminate. With this configuration, the optical connector, such as the connector 55 of FIG. 2, which is used on prior art endoscopes, is eliminated, thereby reducing weight and increasing light transmission efficiency.

With reference to FIGS. 20 and 21, the rearward member 542 of the hand-operated control means is pivotally mounted to the body piece by the pivot axle 635 and extends above pivot point 544 to form an actuation means comprising a first and second "L"-shaped tines, 640 and 645 respectively, which lie below the aperture in the bore 650. Insertion of the instrument into the bore and clockwise rotation 655 of the instrument engages each bayonet 605 in the terminal detent 660 of its corresponding twist-lock slot 600 and rotates the drive pin 585 to a position between the tines 640 and 645. Alignment of the tines and the pin is ensured prior to insertion of the instrument by closing the hand control means; the operative elements of the instrument must be closed in order for the instrument to be inserted into its bore. Thenceforth, closure of the hand-operated control means causes the second tine 645 to apply a rearward pressure on the drive pin, which pulls the drive rod in a rearward direction, causing closure of the operative elements 555. Conversely, when the hand-operated control means is opened, the frist tine 640 moves the drive rod forward, opening the operative elements. Counterclockwise rotation of the instrument disengages the bayonets 605 and causes the drive pin to swing clear of the tines and to be aligned with the slot 650 in the instrument bore 255, through which it passes when the instrument is removed or inserted.

The embodiment described in FIGS. 17 through 21 may be used with a cannula inserted through a body surface such as the abdominal wall, or may be used without a cannula, for example, when inserted through a natural orifice such as the mouth, nose, or rectum, or through an opening in the skin, for example, as in cosmetic or thoracoscopic endosurgery. Additionally, the embodiment of FIGS. 17 through 21 may be used without the attached display, in which circumstance the surgeon observes the image on a conventional monitor. Although enhanced presence is not provided in this mode, the surgeon benefits by operating the instrument and the endoscope with one hand.

Figure 22:
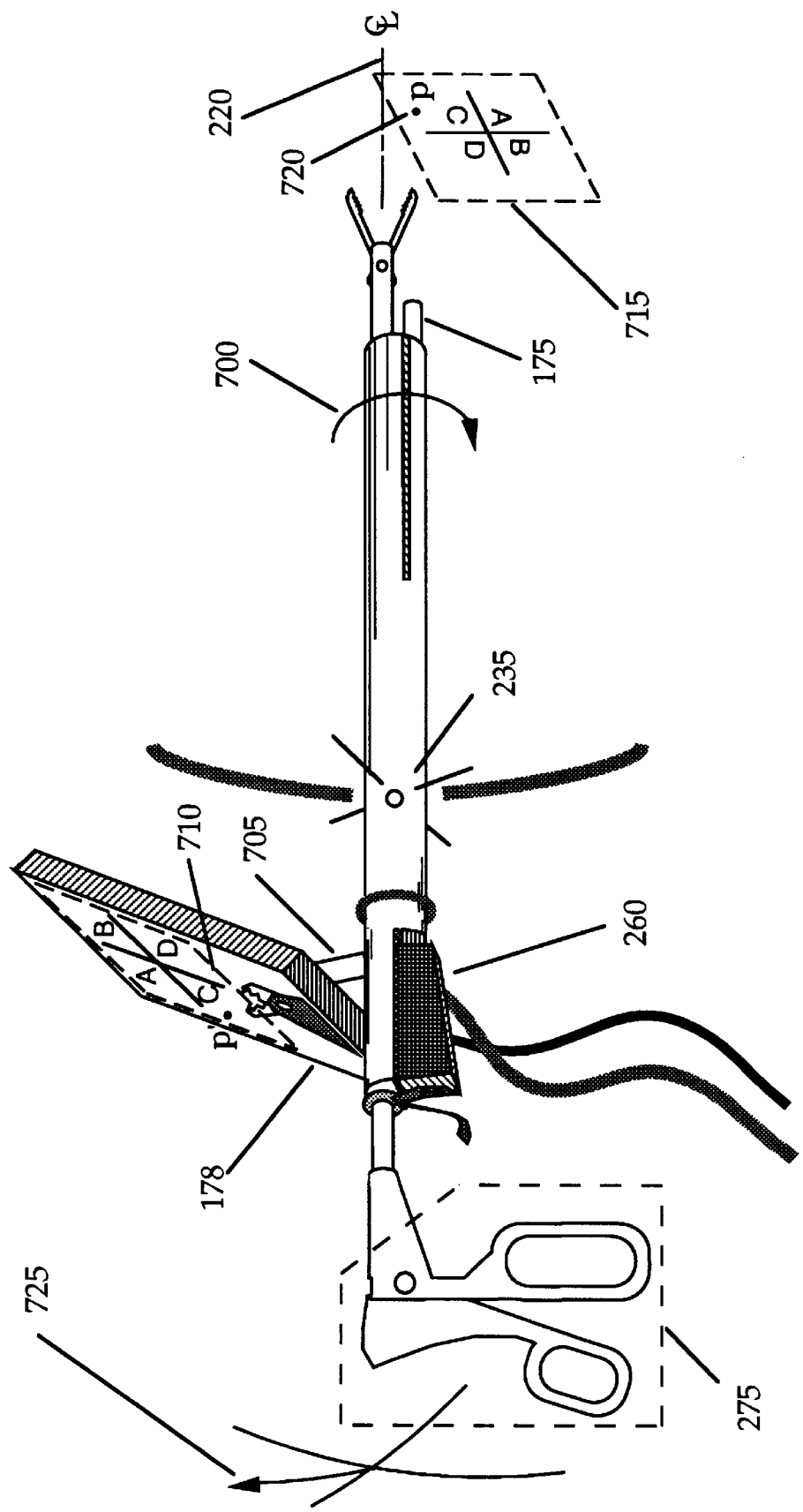
FIG. 22 is a perspective view of the endoscopic surgery system of FIG. 8 wherein the endoscope and video camera has been rotated about the axis of the endosurgical instrument, to a position beneath said instrument and an inverted orientation.

In FIG. 22 an embodiment of the present invention is disclosed which is directed to overcoming a well-known impediment of laparoscopic surgery—that operating through a port in the abdominal wall introduces a fulcrum at the insertion point 235, so that the instrument handle must be moved in the opposite direction of that which the instrument distal tip is desired to move. The FIG. 22 embodiment differs from that of FIGS. 6 and 8 in that the endoscope 175 and video camera head 260 are beneath the instrument rather than above it. This repositioning is achieved by rotating the insertion tube, endoscope, and camera head around the instrument axis 220 as a unit, as indicated by arrow 700. The display 178 is removed and reattached at a location 705 on the surface of the insertion tube opposite to that of the video camera head. In this embodiment, the image 710 of the distal instrument tip occupies the same position in the image field as in the FIGS. 6 and 8 embodiment, however, the image of the object field is inverted, as indicated by object matrix ABCD 715 and its displayed image 710. Accordingly, to cause the image of the instrument tip to move toward a selected image point p' 720, the operator would move the instrument handle 275 generally toward that point in the display, as indicated by vector 725. The system is thereby caused to rotate about the fulcrum point, and the distal tip moves toward corresponding object point p 720, which is indicated in the display as movement toward p'. Thereby, reversal of instrument movement has been corrected and management of the instrument is now closer to that experienced in conventional open surgery, although the object field is inverted in the image.

With reference to FIGS. 23 and 24, a means is provided by which the embodiments of FIGS. 8 and 22 can be combined in a single system, the mode of operation being selectable by the operator. The object is to provide for rotation about the instrument axis 220 of the insertion tube, endoscope, and camera as a single unit while maintaining the display in the upright position. With reference to the distal view of FIG. 23, this embodiment comprises an insertion tube 190 with endoscope and instrument bores 250 and 255 respectively, the proximal portion of which tube is indicated in the drawing, a coupling member 730, a coupling member cover 735, a proximal instrument tube 740, a threaded retainer ring 745, a first semicylindrical mounting element 750 to which is attached a post 330, with attached ball 335 for adjustably securing a display, if an attached display is used, and a second semicylindrical mounting element 755 to which is attached an instrument retaining latch 395.

The position of the video camera head 260 on the insertion tube is indicated in the drawing. Just distal to the recessed plateau 350 on which the camera head lies is a circumferential groove 760 which mates with the semicircular surface 765 at the distal end of the conical portion 770 of the coupling member 730. The coupling member comprises said conical portion and a proximal cylindrical portion 775, the circumferential surface 780 of which is knurled to provide a finger gripe for rotation of said member. A clearance bore 785 is provided through the cylindrical portion 775 for passage of the instrument. A second bore 790 is provided for passage of the camera's electrical cable. A semicircular groove 795 is provided in the distal face of the cylindrical portion, which mates with the proximal end of the insertion tube 190. A pin 800 is provided on the interior of the semicircular surface 765 which mates with a bore 805 within the circumferential groove 760 in the insertion tube to prevent rotation of the coupling member 730 with respect to the insertion tube 190. After insertion of the insertion tube into the coupling member, the coupling member cover 735 is secured into place with screws 815, thereby firmly securing the insertion tube against movement with respect to the coupling member.

Referring to FIGS. 23 and 24, the instrument tube 740, is inserted into the cylindrical recess 820 in the proximal face of the cylindrical portion 775 of the coupling member 730. The threaded retainer ring 745 is passed over the proximal insertion tube, which has an inner diameter less than that of the collet 825 of the instrument tube. The retainer ring is threaded into the cylindrical portion of the coupling member until it presses the collet against the cylindrical portion of the coupling member with enough force to resist, but not prevent, rotation of the instrument tube in the cylindrical recess. A detent mechanism is provided by or more spherical pits 830 on the end surface of the cylindrical recess 820, radially positioned so as to nest with a spring-loaded spherical bead 835 affixed to the distal surface of instrument tube 740. The detent mechanism releasably secures the instrument tube at selected rotational positions. In particular, two diametrically opposed pits can be used to stabilize the system for operation in the modes of FIG. 8 and FIG. 22.

The semicylindrical mounting elements 750 and 755, which have inner diameters equal to the outer diameter of the instrument tube, are affixed to each other by screws or an adhesive, securing the instrument tube therebetween.

FIG. 25 illustrates the orientation of the coupling member 730 and insertion tube 190 for operation according to the mode of FIG. 8. Rotation of these elements about the instrument axis 220, as indicated by vector 837, converts the instrument to the mode of FIG. 22, which is depicted in FIG. 26. To change between operating modes, the operator grasps the instrument tube, display mount, or display with one hand and with the other hand grasps the knurled surface of the coupling member, rotating it one-half turn.

The embodiments illustrated in FIGS. 6, 8, and 22 through 26 provide for axially securing the instrument to the insertion tube by means of a retaining latch. Thereby, the endoscope, video camera, and display move in and out in synchrony with the advancement and withdrawal of the instrument. It is also within the scope of this invention to operate in a manner in which the endoscope, video camera, and display are fixed at a selected degree of insertion and the instrument, with the instrument latch disengaged or absent, is advanced and withdrawn independently. This may be effected by omitting the cannula of FIG. 9 and, as illustrated in FIG. 6, passing the insertion tube directly through a port made in the body wall. Alternatively, in another embodiment of this invention, a cannula, illustrated in FIGS. 27 through 30, is employed which provides for securing the insertion tube at any desired degree of insertion. FIG. 27 shows a thumbwheel/cam 840 comprising a disk with an excentric axle 870, which disk is provided with a detent 845 and a roughened edge portion 850 that provides friction for finger operation. FIG. 28 shows a cannula 855, with the thumbwheel/cam 840 of FIG. 27 mounted thereon by a means of a post 860 affixed to the proximal end 865 of the cannula and an axle 870. FIG. 29 shows a side view of the cannula and thumbwheel/cam 840, post 860, and axle 870. A slot 875 is provided in the wall of the cannula, which allows clear passage of the thumbwheel into the cannula bore 880. The thumbwheel/cam in shown in the disengaged position. A shaft 885, such as an insertion tube, is shown within the bore, the shaft being free to move within said bore. Rotation of the thumbwheel/cam, as indicated by vector 890 in FIG. 28, causes the thumb wheel/cam to enter the bore and press on the shaft at point 900, forcing it against the opposite wall of the bore at point 895, thereby preventing it from moving within the bore, as illustrated in FIG. 30. The detent 845 on the thumbwheel/cam prevents inadvertent release of the shaft.

FIGS. 31 through 33 illustrate another embodiment of the present invention wherein an elevated perspective is provided of the tip of a surgical instrument, for example an instrument inserted through the instrument bore of the embodiments of FIGS. 8 and 22. FIG. 31 shows an insertion tube 190 with endoscope 905. The endoscope is provided with a periscopic distal element 910. The endoscope, which may be rotated within its bore in the insertion tube, is shown, in FIG. 31, positioned so that periscopic distal element lies adjacent to the distal end 355 of the insertion tube, overlaying the instrument bore. The length of said periscopic distal element is selected so that it does not extend beyond the area of said distal face, thereby, it does not impede passage of the insertion tube through a cannula and into the body. After insertion, the endoscope is rotated one-half turn, which may be accomplished by grasping the optical connector 55 and turning it according to vectors 915 and 920.

Referring now to FIG. 32, after rotation of the endoscope the entrance pupil 925 of the endoscope is above the level of the insertion tube, affording an elevated perspective of the distal tip 380 of the instrument, which may now be inserted through the unblocked instrument bore 255 in the insertion tube.

FIG. 33 is a detailed cut-away view of the distal portion of the endoscope, showing the optical components therein. Prisms 930 and 935 redirect the optical axis 940 from the entrance pupil 925 to the main optical tube 905 of the endoscope. Lenses 945 and 950 refocus the image for transmission through the endoscope. The well known principles of endoscope design may be readily adapted to the design of this embodiment. The objective lens 955 is positioned at the entrance pupil. Illumination of the field of view is provided through optical fibers 960 which terminate in an illumination window 965 below the entrance pupil.

Figure 34:
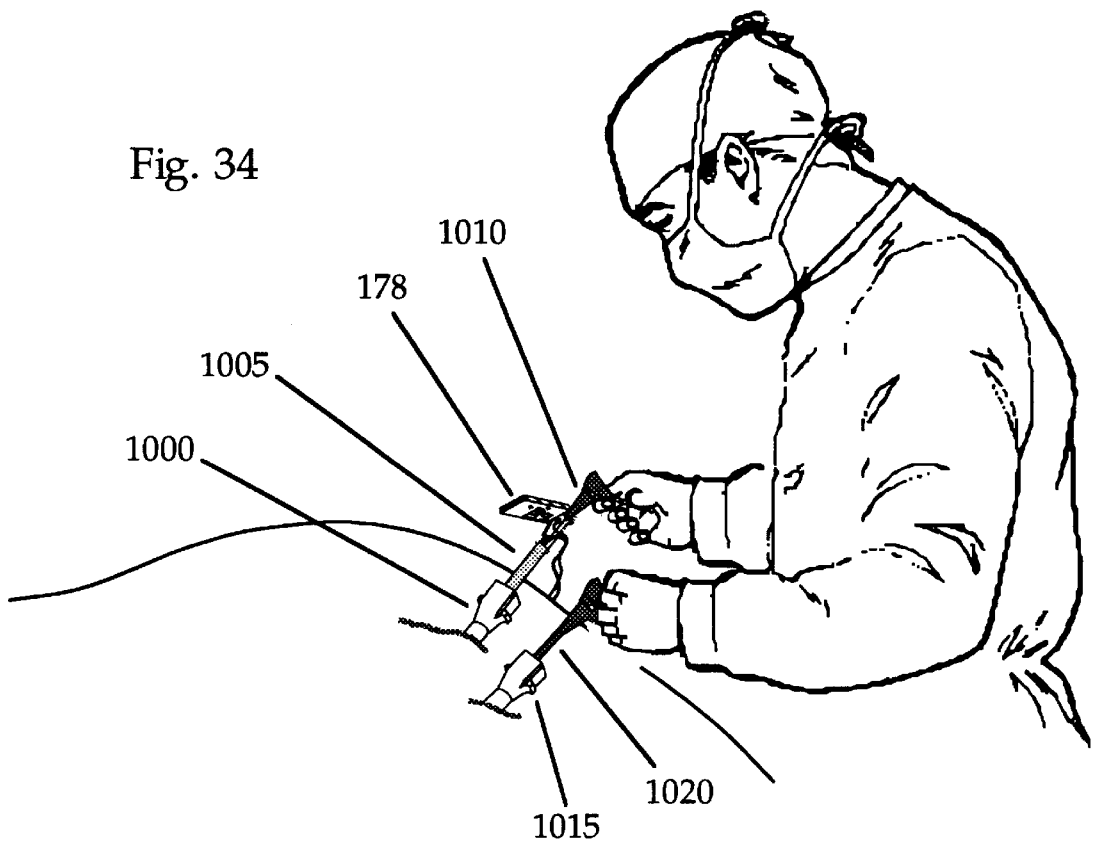
FIG. 34 depicts the endosurgical instrument, video endoscope, insertion tube, and cannula of FIGS. 8 through 13 used in combination with a video monitor by a surgeon operating with an instrument in each hand.

The embodiments of FIGS. 8 through 13 and 22 through 33 may be employed to carry out a laparoscopic surgical procedure with enhanced dexterity and enhanced presence. With reference to FIG. 34, the surgeon inserts the cannula of FIG. 9, here designated 1000, through the abdominal wall and then inserts therethrough the FIG. 8 embodiment of the present invention, here designated 1005. The surgeon then selects an instrument 1010 and inserts it through the instrument bore (255 of FIG. 8) until it is axially secured by the latch (395 of FIG. 8). If two handed surgery is contemplated, a second port is established with a cannula 1015 of conventional design and an instrument 1020 of conventional design is inserted therethrough. Other ports in the abdominal wall for instruments operated by other persons may be established as desired. The surgeon views the endoscopic image on display 178, which image shows the tip of instrument 1010, the adjacent tissues and the tip of instrument 1020 when it within the field of view.

Figure 35:
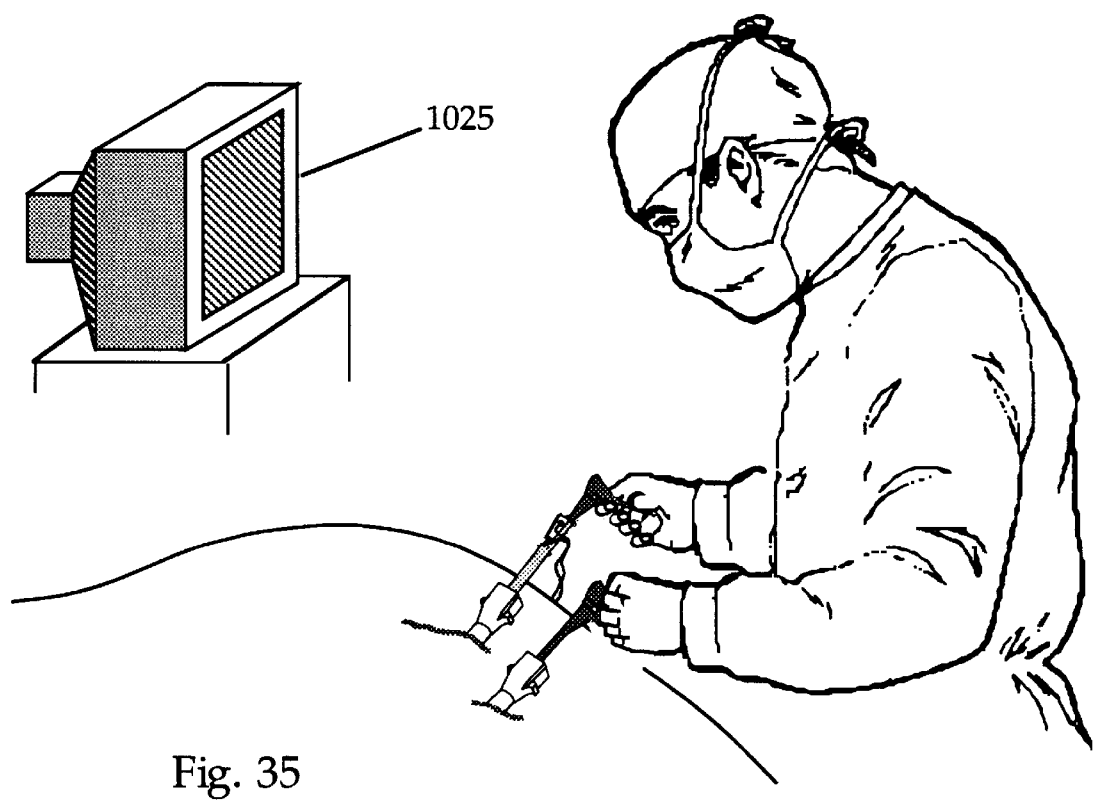
FIG. 35 depicts the endosurgical instrument, video endoscope, insertion tube, video display, and cannula of FIGS. 8 through 13 used in combination by a surgeon operating with an instrument in each hand.

With reference to FIG. 35, a laparoscopic surgical procedure can also be carried out with the display 178 removed, turned off, or ignored. Set up is the same as described with respect to FIG. 34, except that a separate monitor 1025 is provided in accordance with the prior art practice of laparoscopic surgery. Although enhance presence is not provided, this configuration does enable the surgeon to operate with an instrument in each hand while simultaneously, and without conscious effort, keeping the laparoscope directed at all times to the operating site.

In all of the foregoing embodiments, the size of the image as compared with the dimensions of the actual object field may be readily modified to accommodate the operator's preference, either by altering the endoscope optics or by electronically scaling the video image; both are within the scope of the present invention.

In all of the foregoing embodiments, the use of monoscopic video has been indicated, wherein monoscopic means that a single two-dimensional image is formed and presented to both eyes. Stereoscopic video endoscopy is well known in the art and the substitution of stereoscopic for monoscopic video is within the scope of all of the embodiments of this invention. Stereoscopic video endoscopes made by Richard Wolf Medical Instruments, in Rosemont, utilizes time-sequential presentation of left- and right-eye images derived from special endoscopes with side-by-side optical channels.

The operator wears special glasses with electrically switchable transmissivity. The left and right windows are made alternately transparent and opaque in synchrony with the images from each side of the laparoscope. Stereoscopic imaging with a monoscopic endoscope and special signal processing is sold by Automated Medical Products Corp. of New York, N.Y. Stereoscopic video projection of the virtual image to an arbitrary region behind the display is well known and readily achieved by adjusting the relative left/right positions of the left-eye and right-eye images as they appear in the display, using known video signal processing methods. In this manner, substitution of stereoscopic video in the present invention enables the operator to perceive the image of the instrument tip and the tissues to lie behind the display, for example, in substantially the same spatial position in which they would be observed were they directly visible. This enhances the illusion of reaching into an operative site under direct visualization, which further facilitates dexterous manipulation. If stereoscopic imaging is used, the display may be set perpendicular to the instrument axis, and ambiguity as to direction and motion will be reduced as compared to a monoscopic display.

Endoscopes are made that have fields of view that are symmetric about the endoscope axis ("straight ahead" or "0°" endoscopes) and that have angularly offset fields of view (e.g., "30°" and "70°" endoscopes). The use of straight-ahead and angled endoscopes are both within the scope of the present invention.

Whereas in the illustrated embodiments only rigid endoscopes are shown, it is understood that embodiments incorporating flexible endoscopes and flexible endoscopic instruments which pass therethrough are within the scope of this invention.

Whereas endoscopes and instruments of specific dimensions have been selected so as to illustrate preferred embodiments for certain medical applications, the invention is not limited as to endoscopes and instruments of these sizes. In particular, smaller endoscopes and instruments will be found to be preferable for other medical applications.

Whereas, in the foregoing, hand-powered grasping and cutting instruments have been shown, this invention is not limited with regard to the types of instruments that may be utilized, which also include but are not limited to articulated or flexible hand-powered instruments, electrocautery and laser photocoagulation devices, suctioning devices for the evacuation of fluids and soft tissues, and mechanically powered devices for removal of soft and hard tissues, which may, for example, be rotary or oscillatory in motion and driven by pneumatic or hydraulic means or by electrical or ultrasonic motors. The hand operated control means may be, for example, in the form of a pistol grip with a trigger that actuates electrically or mechanically controlled instruments.

Whereas, it is desirable to make the weight and inertia of the hand-held instrument portion of this invention as low as possible, all measures to reduce its size and mass, such as the use of special light-weight materials, the removal of electronic modules from the hand-held instrument to the electronics units, and the reduction in size of any or all of its components is within the scope of this invention.

Although the present invention has been shown and described with respect to preferred embodiments, the foregoing and other changes and modifications which are obvious to a person skilled in the art to which the invention pertains are deemed to be within the spirit and scope of the invention.

I claim:

1. An endoscopic surgical instrument for use in endoscopic surgery comprising:

an elongated insertion shaft including a distal end-effector and an opposite proximal end;

an insertion tube configured to receive the elongated insertion shaft therethrough;

a handle portion operably coupled to the proximal end and configured to manually manipulate the end-effector during endoscopic surgery;

a video endoscope component coupled to the shaft having a distal viewing face positioned rearward of the distal end effector to view the distal end-effector from a position along said shaft; and a video display device operably coupled to the endoscope component and coupled to said insertion tube proximate and adjacent to the proximal end of said shaft at a viewing angle and location therealong such that an image of the end-effector displayed on said display device appears to be a substantially direct view of said end-effector that is positioned in-line with the insertion shaft.

2. The endoscopic surgical instrument according to claim 1 wherein, the endoscope component is secured to the insertion tube such that the distal viewing face of the endoscope component is proximate to the distal end of the insertion tube; and the elongated insertion shaft of the surgical instrument is mounted such that the end-effector lies distal to the distal ends of the insertion tube and endoscope component.

3. The endoscopic surgical instrument according to claim 2 further including:

a cannula device arranged to receive the insertion tube therethrough; and a rotation preventing mechanism adapted to substantially prevent rotation of the insertion tube within the cannula while allowing axial translation of the insertion tube relative to the cannula.

4. The endoscopic surgical instrument according to claim 3 wherein, the rotation preventing mechanism comprises mating longitudinal groove and raised bar components affixed to the cannula and the insertion tube.

5. The endoscopic surgical instrument according to claim 3 further including:

a rotation mechanism that permits the endoscope component to be rotated about an axis of the instrument in the insertion tube, while maintaining non-rotation between the insertion tube and the cannula, between a first position wherein the endoscope component and the display device are both positioned on the same side relative to the surgical instrument, and a second position wherein the endoscope component and the display device are positioned on substantially opposite sides relative to the surgical instrument.

6. The endoscopic surgical instrument according to claim 1 wherein, the video device is a flat panel display.

7. The endoscopic surgical instrument according to claim 1 further including:

a rotation mechanism that permits the endoscope component to be rotated about an axis of the instrument so as to view the end-effector and the surgical field from at least two perspectives.

8. The endoscopic surgical instrument according to claim 1 further including:

an adjustable mounting mechanism for attaching the video display device to the insertion tube.

9. The endoscopic surgical instrument according to claim 8 wherein, said adjustable mounting mechanism is adapted to releasably mount the display device to the insertion tube.

10. The endoscopic surgical instrument according to claim 1 further including:

a stereographic video imaging forming system for presenting left-eye and right-eye stereoscopic images on the video display device and for making them perceivable as three dimensional images by an operator of the video endoscope component.

11. The endoscopic surgical instrument according to claim 1 further including:

a latching arrangement for releasably latching the received insertion shaft to the insertion tube such that the received insertion shaft rotates freely about its axis within the insertion tube and cannot be advanced or withdrawn.

12. The endoscopic surgical instrument according to claim 11 wherein, said latching arrangement includes an annular element affixed on the insertion shaft proximal to its handle and a spring clip affixed to the insertion tube that engages the annular element when the surgical instrument is fully inserted.

13. The endoscopic surgical instrument according to claim 1 wherein, said endoscope component including a video image detector is situated above the insertion shaft and provides an upright image of the field of view wherein the end-effector is visible in the lower portion of the display device.

14. The endoscopic surgical instrument according to claim 1 further including:

a periscope coupled to the distal end of the endoscope component, the periscope including a substantially distally facing window that is offset relative to the optical path of the endoscope component; and light reflectors for directing the optical path of the endoscope component to the window.

15. The endoscopic surgical instrument according to claim 14 further comprising:

a mechanism for rotating the periscope and endoscope component relative to the insertion tube from a position wherein the periscope is within the area of the distal face of the insertion tube to a position wherein the window of the periscope is outside of the area of the distal face.

16. A video endoscope system for use by a surgeon in endoscopic surgery:

an insertion tube arranged to receive a surgical instrument having an elongated shaft and an end-effector;

an elongated endoscope component received within the insertion tube, the endoscope component being arranged to facilitate viewing of the end-effector of the received surgical instrument;

a video display for displaying an image of the end-effector viewed by the endoscope component coupled proximate a proximal end of said insertion tube; and a handle operably coupled to the surgical instrument for actuation of the end effector, and to the insertion tube for positioning of end-effector and said endoscope component as a unit, independent of the operation of the end-effector and in a manner substantially maintaining said end-effector in the field of view of said endoscope component during operation and manipulation of the handle such that a surgeon operating the endoscope system by the handle will view and perceive the image of the end-effector on the video display as being directly viewed at a true position of the end-effector from the perspective of the surgeon, enabling the surgeon to effectively perform remote surgery with the hand-eye coordination approximating that of open surgery.

17. The endoscopic surgical instrument according to claim 16 wherein, the endoscope component is secured to the insertion tube such that the distal viewing face of the endoscope component is proximate to the distal end of the insertion tube; and the elongated shaft of the surgical instrument is mounted such that the end-effector lies distal to the distal ends of the insertion tube and endoscope component.

18. The endoscopic surgical instrument according to claim 16 wherein, the video display is a flat panel display.

19. The endoscopic surgical instrument according to claim 16 further including:

a rotation mechanism that permits the endoscope component to be rotated substantially about an axis of the instrument so as to view the end-effector and the surgical field from at least two perspectives.

20. The endoscopic surgical instrument according to claim 16 further including:

an adjustable mounting mechanism for attaching the video display to the insertion tube.

21. The endoscopic surgical instrument according to claim 20 wherein, said adjustable mounting mechanism is adapted to releasably mount the display to the insertion tube.

22. The endoscopic surgical instrument according to claim 16 further including:

a stereographic video imaging forming system for presenting left-eye and right-eye stereoscopic images on the video display and for making them perceivable as three dimensional images by an operator of the endoscope component.

23. The endoscopic surgical instrument according to claim 16 further including:

a latching arrangement for releasably latching the received insertion shaft to the insertion tube such that the received insertion shaft rotates freely about its axis within the insertion tube and cannot be advanced or withdrawn.

24. The endoscopic surgical instrument according to claim 23 wherein, said latching arrangement includes an annular element affixed on the insertion shaft proximal to its handle and a spring clip affixed to the insertion tube that engages the annular element when the surgical instrument is fully inserted.

25. The endoscopic surgical instrument according to claim 16 wherein, said endoscope component including a video image detector is situated above the shaft and provides an upright image of the field of view wherein the end-effector is visible in the lower portion of the display.

26. The endoscopic surgical instrument according to claim 16 further including:
- a periscope coupled to the distal end of the elongated endoscope component, the periscope including a substantially distally facing window that is offset relative to the optical path of the elongated endoscope component; and
- light reflectors for directing the optical path of the elongated endoscope component to the window.

27. The endoscopic surgical instrument according to claim 26 further comprising:
- a mechanism for rotating the periscope and endoscope component relative to the insertion tube from a position wherein the periscope is within the area of the distal face of the insertion tube to a position wherein the window of the periscope is outside of the area of the distal face.

28. The endoscopic surgical instrument according to claim 16 wherein,
- said handle is mounted to the proximal end of the elongated shaft.

29. An endoscopic surgical instrument for use in endoscopic surgery comprising:
- an elongated insertion shaft including a distal end-effector and an opposite proximal end;
- a handle portion operably coupled to the proximal end and configured to manually manipulate the end-effector during endoscopic surgery;
- a video endoscope component coupled to the shaft having a distal viewing face positioned rearward of the distal end effector to view the distal end-effector from a position along said shaft;
- a video display device operably coupled to the endoscope component and mounted proximate and adjacent to the proximal end of said shaft at a viewing angle and location therealong such that an image of the end-effector displayed on said display device appears to be a substantially direct view of said end-effector that is positioned in-line with the insertion shaft;
- an elongated insertion tube configured to receive the elongated insertion shaft therethrough;
- a cannula device arranged to receive the insertion tube therethrough; and
- a rotation preventing mechanism adapted to substantially prevent rotation of the insertion tube within the cannula while allowing axial translation of the insertion tube relative to the cannula.

30. The endoscopic surgical instrument according to claim 29 wherein,
- the rotation preventing mechanism comprises mating longitudinal groove and raised bar components affixed to the cannula and the insertion tube.

31. The endoscopic surgical instrument according to claim 29 further including:
- a rotation mechanism that permits the endoscopic component to be rotated about an axis of the instrument in the insertion tube, while maintaining non-rotation between the insertion tube and the cannula, between a first position wherein the endoscope component and the display are both positioned on the same side relative to the surgical instrument, and a second position wherein the endoscope component and the display are positioned on substantially opposite sides relative to the surgical instrument.

32. A method of performing endoscopic surgery comprising the steps of:
- inserting into a body part through a natural orifice or incision an insertion tube;
- positioning through said tube a surgical instrument having an elongated shaft and an end effector;
- viewing an image of the end effector from an endoscope component received within the insertion tube and arranged to facilitate viewing of the end-effector of the received surgical instrument;
- displaying the image of the end effector on a video display coupled proximate a proximal end of said insertion tube; and
- operating a handle operably coupled to the surgical instrument for actuation of the end effector, and to the insertion tube for positioning of said end-effector and said endoscope component as a unit, independent of operation of the end-effector and in a manner substantially maintaining said end-effector in the field of view of said endoscope component during operation and manipulation of the handle such that a surgeon operating the endoscope system by the handle will view and perceive the image of the end-effector on the video display as being directly viewed at a true position of the end-effector from the perspective of the surgeon, enabling the surgeon to effectively perform remote surgery with the hand-eye coordination approximating that of open surgery.

33. The method of claim 32 further including the step of:
releasably latching the received insertion shaft to the insertion tube such that the received insertion shaft rotates freely about its axis within the insertion tube and cannot be advanced or withdrawn.

34. The method of claim 32 further including the step of:
releasably mounting the display device to the insertion tube.

35. The method of claim 32 further including the step of:
rotating the endoscope component substantially about an axis of the instrument so as to view the end-effector and the surgical field from at least two perspectives.

* * * * *